(12) United States Patent
Bhatia

(10) Patent No.: US 9,650,678 B2
(45) Date of Patent: May 16, 2017

(54) METHODS FOR IDENTIFYING AN INCREASED RISK OF ANTHRACYCLINE-RELATED CARDIOTOXICITY

(71) Applicant: CITY OF HOPE, Duarte, CA (US)

(72) Inventor: Smita Bhatia, Arcadia, CA (US)

(73) Assignee: CITY OF HOPE, Duarte, CA (US)

( * ) Notice: Subject to any disclaimer, the term of this patent is extended or adjusted under 35 U.S.C. 154(b) by 177 days.

(21) Appl. No.: 14/101,006

(22) Filed: Dec. 9, 2013

(65) Prior Publication Data

US 2014/0171382 A1 Jun. 19, 2014

Related U.S. Application Data

(60) Provisional application No. 61/734,778, filed on Dec. 7, 2012.

(51) Int. Cl.
| | | |
|---|---|---|
| *C12Q 1/68* | (2006.01) | |
| *A61K 45/06* | (2006.01) | |
| *A61K 31/704* | (2006.01) | |
| *A61K 31/136* | (2006.01) | |

(52) U.S. Cl.
CPC .......... *C12Q 1/6886* (2013.01); *A61K 31/136* (2013.01); *A61K 31/704* (2013.01); *A61K 45/06* (2013.01); *C12Q 2600/106* (2013.01); *C12Q 2600/156* (2013.01)

(58) Field of Classification Search
None
See application file for complete search history.

(56) References Cited

PUBLICATIONS

Blanco et al; Journal of Clinical Oncology, vol. 28, sup abstract 9512; 2010.*
ss1356725695 (for rs2232228; dbSNP, NCBI, NLM, 2014).*
ss4929686 (for rs2232228, dbSNP, NCBI, NLM, 2002).*
Olson, R. D., et al., "Doxorubicin Cardiotoxicity May Be Caused by Its Metabolite, Doxorubicinol," Proc. Natl. Acad. Sci. USA 85:3585-3589 (1988).
Perik, P. J., et al., "The Dilemma of the Strive for Apoptosis in Oncology: Mind the Heart," Crit. Rev. Oncol. Hematol. 53:101-113 (2005).
Puma, N., et al., "Anthracycline-Related Cardiotoxicity: Risk Factors and Therapeutic Options in Childhood Cancers," Signa Vitae 3(1):30-34 (2008).
Purcell, S., et al., "PLINK: A Tool Set for Whole-Genome Association and Population-Based Linkage Analyses," Am. J. Hum. Genet. 81:559-575 (2007).
Shankar, S. M., et al., "Monitoring for Cardiovascular Disease in Survivors of Childhood Cancer: Report from the Cardiovascular Disease Task Force of the Children's Oncology Group," Pediatrics 121:e387 (2008).
Spicer, A. P., et al., "Hyaluronan and Morphogenesis," Birth Defects Res. (Part C) 72:89-108 (2004).
Stewart, D. J., et al., "Concentrations of Doxorubicin and Its Metabolites in Human Autopsy Heart and Other Tissues," Anticancer Res. 13:1945-1952 (1993).
Toole, B.P., "Hyaluronan and Its Binding Proteins, the Hyaladherins," Curr. Opin. Cell Biol. 2:839-844 (1990).
Vanderweele, T. J., et al., "Case-Only Gene-Environment Interaction Studies: When Does Association Imply Mechanistic Interaction?" Genet. Epidemiol. 34(4):327-334 (2010).
Visscher, H., et al., "Pharmacogenomic Prediction of Anthracycline-Induced Cardiotoxicity in Children," J. Clin. Oncol. 30(13):1422-1428 (2012).
Waldenstrom, A., et al., "Accumulation of Hyaluronan and Tissue Edema in Experimental Myocardial Infarction," J. Clin. Invest. 88:1622-1628 (1991).
West, D. C., et al., "Angiogenesis Induced by Degradation Products of Hyaluronic Acid," Science 228:1324-1326 (1985).
Wojnowski, L., et al., "NAD(P)H Oxidase and Multidrug Resistance Protein Genetic Polymorphisms are Associated with Doxorubicin-Induced Cardiotoxicity," Circulation 112:3754-3762 (2005).
Wouters, K. A., et al., "Protecting Against Anthracycline-Induced Myocardial Damage: A Review of the Most Promising Strategies," Br. J. Haematol. 131:561-578 (2005).
Zhang, J., et al., "Identification of the Promoter of Human Carbonyl Reductase 3 (CBR3) and Impact of Common Promoter Polymorphisms on Hepatic CBR3 mRNA Expression," Pharm. Res. 26(9):2209-2215 (2009).
Zhang, W., et al., "Glucocorticoids Induce a Near-Total Suppression of Hyaluronan Synthase mRNA in Dermal Fibroblasts and in Osteoblasts: A Molecular Mechanism Contributing to Organ Atrophy," Biochem. J. 349:91-97 (2000).
Anderson, C. D., et al., "The Effect of Survival Bias on Case-Control Genetic Association Studies of Highly Lethal Diseases," Circ. Cardiovasc. Genet. 4(2):188-196 (2011).
Armenian, S. H., et al., "Incidence and Predictors of Congestive Heart Failure After Autologous Hematopoietic Cell Transplantation," Blood 118:6023-6029 (2011).
Bai, K.J., et al., "The Role of Hyaluronan Synthase 3 in Ventilator-Induced Lung Injury," Am. J. Respir. Crit. Care Med. 172:92-98 (2005).
Bains, O. S., et al., "Naturally Occurring Variants of Human CBR3 After Anthracycline in Vitro Metabolism," J. Pharmacol. Exp. Ther. 332(3):755-763 (2010).
Begg, C. B., et al., "Statistical Analysis of Molecular Epidemiology Studies Employing Case-Series," Cancer Epidemiol. Biomarkers Prev. 3:173-175 (1994).

(Continued)

*Primary Examiner* — Jehanne Sitton
(74) *Attorney, Agent, or Firm* — Perkins Coie LLP; Lara J. Dueppen

(57) ABSTRACT

Methods of identifying a subject having an increased risk of developing anthracycline-related cardiotoxicity are provided. Such methods may include isolating a DNA sample from a biological specimen from the subject; genotyping the DNA sample to determine a copy number of a variant allele that increases the risk of developing chemotherapy-induced cardiotoxicity; and identifying the subject as having an increased risk of developing anthracycline-related cardiotoxicity when the copy number is at least one. In some embodiments, the methods may include optimally administering a therapeutically effective dose of a chemotherapy agent or an alternative non-cardiotoxic chemotherapeutic agent to the subject.

10 Claims, 18 Drawing Sheets

(56) References Cited

PUBLICATIONS

Blanco, J. G., et al., "Genetic Polymorphisms in the Carbonyl Reductase 3 Gene CBR3 and the NAD(P)H:Quinone Oxidoreductase 1 Gene NQO1 in Patients Who Developed Anthracycline-Related Congestive Heart Failure After Childhood Cancer," Cancer 112(12):2789-2795 (2008).

Blanco, J. G., et al., "Anthracycline-Related Cardiomyopathy After Childhood Cancer: Role of Polymorphisms in Carbonyl Reductase Genes—A Report from the Children's Oncology Group," J. Clin. Oncol. 30(13):1415-1421 (2012).

Boucek, R. J., et al., "The Major Metabolite of Doxorubicin Is a Potent Inhibitor of Membrane-Associated Ion Pumps," J. Biol. Chem. 262(33):15851-15856 (1987).

Bourguignon, L. Y.W., et al., "Interaction of Low Molecular Weight Hyaluronan (LMW-HA) with CD44 and Toll-Like Receptors Promotes the Actin Filament-Associated Protein (AFAP-110)-Actin Binding and MyD88-NFkB Signaling Leading to Pro-Inflammatory CytokinelChemokine Production and Breast Tumor Invasion," Cytoskeleton (Hoboken) 68 (12):671-693 (2011).

Bryant, J., et al., "Cardioprotection Against the Toxic Effects of Anthracyclines Given to Children with Cancer: A Systematic Review," Health Technol. Assess. 11:1-84 (2007).

Burlew, B. S., et al., "Connective Tissue and the Heart: Functional Significance and Regulatory Mechanisms," Cardiol. Clin. 18(3):435-442 (2000).

Cappola, T. P., et al., "Common Variants in HSPB7 and FRMD4B Associated with Advanced Heart Failure," Circ. Cardiovasc. Genet 3(2):147-154 (2010).

Corda, S., et al., "Extracellular Matrix and Growth Factors During Heart Growth," Heart Failure Reviews 5:119-130 (2000).

De Bakker, P. I. W., et al., "Transferability of Tag SNPs in Genetic Association Studies in Multiple Populations," Nat. Genet. 38(11):1298-1303 (2006).

Ebert, B., et al., "Regulation of Human Carbonyl Reductase 3 (CBR3; SDR21C2) Expression by Nrf2 in Cultured Cancer Cells," Biochem. 49:8499-8511 (2010).

Forrest, G. L., et al., "Human Carbonyl Reductase Overexpression in the Heart Advances the Development of Doxorubicin-Induced Cardiotoxicity in Transgenic Mice," Cancer Res. 60:5158-5164 (2000).

Gianni, L., et al., "Anthracycline Cardiotoxicity: From Bench to Bedside," J. Clin. Oncol. 26(22):3777-3784 (2008).

Gonzalez-Covarrubias, V., et al., "Pharmacogenetics of Human Carbonyl Reductase 1 (CBR1) in Livers from Black and White Donors," Drug Metab. Dispos. 37(2):400-407 (2009).

Granowetter, L., et al., "Dose-Intensified Compared with Standard Chemotherapy for Nonmetastatic Ewing Sarcoma Family of Tumors: A Children's Oncology Group Study," J. Clin. Oncol. 27(15):2536-2541 (2009).

Grenier, M. A., et al., "Epidemiology in Anthracycline Cardiotoxicity in Children and Adults," Semin. Oncol. 25(suppl. 10):72-85 (1998).

Grier, H. E., et al., "Addition of Ifosfamide and Etoposide to Standard Chemotherapy for Ewing's Sarcoma and Primitive Neuroectodermal Tumor of Bone," New Engl. J. Med. 348:694-701 (2003).

Hellman, U., et al., "Parallel Up-Regulation of FGF-2 and Hyaluronan During Development of Cardiac Hypertrophy in Rat," Cell Tissue Res. 332:49-56 (2008).

Hernan, M. A., et al., "A Structural Approach to Selection Bias," Epidemiol. 15:615-625 (2004).

Jacobson, A., et al., "Expression of Human Hyaluronan Synthases in Response to External Stimuli," Biochem. J. 348:29-35 (2000).

Jiang, D., et al., "Regulation of Lung Injury and Repair by Toll-Like Receptors and Hyaluronan," Nat. Med. 11(11):1173-1179 (2005).

Joerger, M., et al., "Pharmacokinetics of Low-Dose Doxorubicin and Metabolites in Patients with AIDS-Related Kaposi Sarcoma," Cancer Chemother Pharmacol. 55:488-496 (2005).

Johnson, S. A., et al., "Antracyclines in Haematology: Pharmacokinetics and Clinical Studies," Blood Rev. 12:52-71 (1998).

Kalabus, J. L., et al., "Expression of the Anthracycline-Metabolizing Enzyme Carbonyl Reductase 1 in Hearts from Donors with Down Syndrome," Drug Metab. Dispos. 38(12):2096-2099 (2010).

Keating, B. J., et al., "Concept, Design and Implementation of a Cardiovascular Gene-Centric 50 K SNP Array for Large-Scale Genomic Association Studies," PLoS One 3(10):e3583 (2008).

Knudson, C. B., et al., "Hyaluronan-Binding Proteins in Development, Tissue Homeostasis, and Disease," FASEB J. 7:1233-1241 (1993).

Kremer, L. C. M., et al., "Frequency and Risk Factors of Subclinical Cardiotoxicity After Anthracycline Therapy in Children: A Systematic Review," Ann. Oncol. 13:819-829 (2002).

Kremer, L. C.M., et al., "Anthracycline Cardiotoxicity in Children," N. Engl. J. Med. 351:120-121 (2004).

Lakhman, S. S., et al., "Fuctional Significance of a Natural Allelic Variant of Human Carbonyl Reductase 3 (CBR3)," Drug Metab. Dispos. 33(2):254-257 (2005).

Lakhman, S. S., et al., "Functional Characterization of the Promoter of Human Carbonyl Reductase 1 (CBR1). Role of XRE Elements in Mediating the Induction of CBR1 by Ligands of the Aryl Hydrocarbon Receptor," Mol. Pharmacol. 72(3):734-743 (2007).

Laurent, T. C., et al., "Hyaluronan," FASEB J. 6:2397-2404 (1992).

Lehmann, S., et al., "Cardiac Systolic Function Before and After Hematopoietic Stem Cell Transplantation," Bone Marrow Transplant. 26:187-192 (2000).

Lipshultz, S. E., et al., "Chronic Progressive Cardiac Dysfunction Years After Doxorubicin Therapy for Childhood Acute Lymphoblastic Leukemia," J. Clin. Oncol. 23(12):2629-2636 (2005).

McKee, C. M., et al., "Hyaluronan (HA) Fragments Induce Chemokine Gene Expression in Alveolar Macrophages," J. Clin. Invest. 98:2403-2413 (1996).

Meissner, K., et al., "Expression and Localization of P-Glycoprotein in Human Heart: Effects of Cardiomyopathy," J. Histochem. Cytochem. 50(10):1351-1356 (2002).

Menna, P., et al., "Cardiotoxicity of Antitumor Drugs," Chem. Res. Toxicol. 21:978-989 (2008).

Minotti, G., et al., "Anthracyclines: Molecular Advances and Pharmacologic Developments in Antitumor Activity and Cardiotoxicity," Pharmacol. Rev. 56(2):185-229 (2004).

Miranda, C. J., et al., "Hfe Deficiency Increases Susceptibility to Cardiotoxicity and Exacerbates Changes in Iron Metabolism Induced by Doxorubicin," Blood 102:2574-2580 (2003).

Mordente, A., et al., "Anthracycline Secondary Alcohol Metabolite Formation in Human or Rabbit Heart: Biochemical Aspects and Pharmacologic Implications," Biochem. Pharmacol. 66:989-998 (2003).

Mordente, A., et al., "New Developments in Antracycline-Induced Cardiotoxicity," Curr. Med. Chem. 16:1656-1672 (2009).

Mrabat, H., et al., "Inhibition of HA Synthase 3 mRNA Expression, with a Phosphodiesterase 3 Inhibitor, Blocks Lung Injury in a Septic Ventilated Rat Model," Lung 187:233-239 (2009).

Mulrooney, D. A., et al., "Cardiac Outcomes in a Cohort of Adult Survivors of Childhood and Adolescent Cancer: Retrospective Analysis of the Childhood Cancer Survivor Study Cohort," BMJ 339:b4606 (2009).

Mushlin, P. S., et al., "Time-Related Increases in Cardiac Concentrations of Doxorubicinol Could Interact with Doxorubicin to Depress Myocardial Contractile Function," Br. J. Pharmacol. 110:975-982 (1993).

Noble, P. W., et al., "Hyaluronan Fragments Activate an NF-kB/l-kBalpha Autoregulatory Loop in Murine Macrophages," J. Exp. Med. 183:2373-2378 (1996).

Olson, L. E., et al., "Protection from Doxorubicin-Induced Cardiac Toxicity in Mice with a Null Allele of Carbonyl Reductase 1," Cancer Res. 63:6602-6606 (2003).

\* cited by examiner

Figure 1

|  | Odds Ratio (95% CI) | P value |
|---|---|---|
| Gender | | |
| Males | 1.0 | |
| Females | 1.47 (0.9-2.4) | 0.13 |
| Age at Primary Cancer Diagnosis | | |
| Per year increase | 0.99 (0.93-1.04) | 0.59 |
| Chest Radiation | | |
| No | 1.0 | |
| Yes | 4.29 (1.9-9.6) | <0.001 |
| Cumulative Anthracycline Exposure (mg/m$^2$) | | |
| 0 | 1.0 | |
| 1-100 mg/m$^2$ | 1.65 (0.5-5.6)* | |
| 101-150 mg/m$^2$ | 3.85 (1.1-13.9) | |
| 151-200 mg/m$^2$ | 3.69 (1.0-13.6) | |
| 201-250 mg/m$^2$ | 7.23 (2.3-22.5) | |
| 251-300 mg/m$^2$ | 23.47 (7.4-74.2) | P for trend <0.001 |
| 301+ mg/m$^2$ | 27.59 (9.3-82.1) | |

Odds ratios were obtained using multivariate conditional logistic regression.

* Association between anthracycline exposure at 1-100 mg/m$^2$ and cardiomyopathy is not statistically significant

Figure 2

CBR1 and CBR3 Genotypes and Risk of Cardiomyopathy

|  | Cases/Controls | OR (95% CI) | P value |
|---|---|---|---|
| CBR1 1096G>A | | | |
| CBR1:AA or GA | 38/66 | 1.0 | |
| CBR1:GG | 132/246 | 0.81 (0.45-1.47) | 0.49 |
| CBR3 V244M | | | |
| CBR3:AA or GA | 91/191 | 1.0 | |
| CBR3:GG | 78/121 | 1.79 (1.08-2.96) | 0.02 |
| Combination of CBR1 and CBR3 | | | |
| CBR1:AA or GA and/or CBR3:AA or GA | 105/211 | 1.0 | |
| CBR1:GG-CBR3:GG | 64/98 | 1.53 (0.93-2.51) | 0.09 |
| Odds ratios were obtained from conditional logistic regression adjusting for age at diagnosis, gender, chest radiation and cumulative anthracycline exposure (0, 1-100, 101-150, 151-200, 201-250, 251-300, 301+ mg/m$^2$) | | | |

Figure 3

| Variables | Cases (n=170) | Controls (n=317) | P value |
|---|---|---|---|
| Age at Primary Cancer Diagnosis (years) | | | |
| Mean (SD) | 8.3 (6) | 8.2 (6) | 0.67 |
| Median (range) | 7.3 (0-20.7) | 7.6 (0-21.1) | |
| Age at Study Participation (years) | | | |
| Mean (SD) | 17.6 (9) | 20.6 (10) | <0.001 |
| Median (range) | 16.6 (0.4-41) | 18.5 (2.0-49) | |
| Gender | | | |
| Females | 94 (55%) | 155 (49%) | 0.15 |
| Race/ Ethnicity[1] | | | |
| Non-Hispanic whites | 124 (73%) | 252 (79%) | |
| Hispanics | 16 (9%) | 29 (9%) | |
| Blacks | 12 (7%) | 14 (5%) | — |
| Other | 18 (11%) | 22 (7%) | |
| Primary Diagnosis[1] | | | |
| Hodgkin lymphoma | 19 (11%) | 36 (11%) | |
| Non-Hodgkin lymphoma | 21 (12%) | 34 (11%) | |
| Bone tumors | 35 (21%) | 44 (14%) | |
| Soft tissue sarcoma | 20 (12%) | 21 (7%) | |
| Acute lymphoblastic leukemia | 23 (14%) | 93 (29%) | — |
| Acute myeloid leukemia | 19 (11%) | 29 (9%) | |
| Other | 33 (19%) | 60 (19%) | |
| Year of Primary Cancer Diagnosis[1] | | | |
| 1966-1980 | 20 (12%) | 25 (8%) | |
| 1981-1990 | 41 (24%) | 77 (24%) | |
| 1991-2000 | 68 (40%) | 147 (46%) | — |
| 2001-2008 | 41 (24%) | 68 (22%) | |
| Length of Follow-up (years)[1] | | | |
| Mean (SD) | 9.2 (9) | 12.3 (9) | <0.001 |
| Median (range) | 7.0 (0.1-35.1) | 11.2 (0.4-40.3) | |
| Cumulative Anthracycline Exposure (mg/m$^2$) | | | |
| Mean (SD) | 291 (142) | 168 (172) | <0.001 |
| Median (range) | 300 (0-575) | 140 (0-1050) | |
| 0 mg/m$^2$ | 15 (9%) | 93 (29%) | |
| 1-100 mg/m$^2$ | 7 (4%) | 48 (15%) | |
| 101-150 mg/m$^2$ | 7 (4%) | 38 (12%) | |
| 151-200 mg/m$^2$ | 9 (5%) | 25 (8%) | |
| 201-250 mg/m$^2$ | 18 (11%) | 29 (9%) | |
| 251-300 mg/m$^2$ | 33 (19%) | 20 (6%) | |
| ≥301 mg/m$^2$ | 81 (48%) | 64 (20%) | <0.001 |
| Chest Radiation[2] | | | |
| Chest radiation | 42 (25%) | 43 (14%) | <0.001 |

Figure 3 (cont'd)

| Table 1 Characteristics of the Study Population (Continued.) | | | |
|---|---|---|---|
| Variables | Cases (n=170) | Controls (n=317) | P value |
| Genotype Status[3] | | | |
| CBR1 1096G>A | | | |
| AA | 2 (1%) | 5 (2%) | |
| GA | 36 (21%) | 61 (19%) | |
| GG | 132 (78%) | 246 (79%) | 0.94* |
| CBR3 V244M | | | |
| AA | 21 (13%) | 49 (16%) | |
| GA | 70 (41%) | 142 (45%) | |
| GG | 78 (46%) | 121 (39%) | 0.13 |
| Combination of CBR1 and CBR3 | | | |
| Both AA/GA | 24 (14%) | 42 (14%) | |
| CBR1 GG and CBR3 AA/GA | 67 (40%) | 146 (47%) | |
| CBR1 AA/GA and CBR3 GG | 14 (8%) | 23 (7%) | |
| Both GG | 64 (38%) | 98 (32%) | 0.27 |
| Either AA/GA | 105 (62%) | 211 (68%) | |
| Both GG | 64 (38%) | 98 (32%) | 0.09 |

[1] Matching variables. Due to variation in the number of controls per case, the percent of controls and cases in each category of a specific matching variable may not be identical.
[2] Five subjects with unknown chest radiation were excluded.
[3] Nine subjects with non-informative genotypes were excluded.
* Exact p value.

Figure 4

| Variables | Overall (n=170) | Asymptomatic (n=90) | Symptomatic (n=80) | P value |
|---|---|---|---|---|
| Ejection Fraction (%)[1] | | | | |
| Mean (SD) | 41 (11) | 45 (9) | 36 (12) | <0.001 |
| Median (range) | 42 (10-68) | 48 (20-68) | 37 (10-59) | <0.001 |
| EF ≤40% (n[%]) | 62 (46%) | 20 (28%) | 42 (66%) | <0.001 |
| EF >40% (n[%]) | 73 (54%) | 51 (72%) | 22 (34%) | |
| Fractional Shortening (%)[2] | | | | |
| Mean (SD) | 22 (5) | 24 (3) | 19 (7) | <0.001 |
| Median (range) | 24 (5-33) | 24 (12-28) | 20 (5-33) | <0.001 |
| SF ≤28% (n[%]) | 142 (99%) | 86 (100%) | 56 (98%) | |
| SF >28% (n[%]) | 1 (1%) | 0 | 1 (2%) | 0.40* |
| Echocardiographic confirmation of depressed cardiac function with EF ≤40% and/or SF ≤28% | | | | |
| Yes | 166 (98%) | 90 (100%) | 76 (95%) | |
| No | 4 (2%) | 0 | 4 (5%) | 0.05* |
| Echocardiographic confirmation of depressed cardiac function with EF ≤40% and SF ≤28% | | | | |
| Yes | 39 (35%) | 16 (24%) | 23 (53%) | |
| No | 71 (65%) | 51 (76%) | 20 (47%) | 0.002 |
| Echocardiographic confirmation of depressed cardiac function with EF >40% and SF <25% | | | | |
| Yes | 34 (31%) | 25 (37%) | 9 (21%) | |
| No | 76 (69%) | 42 (63%) | 34 (79%) | 0.09 |
| Echocardiographic confirmation of depressed cardiac function with SF 25-28% and EF ≥ 55% | | | | |
| Yes | 5 (5%) | 3 (4%) | 2 (5%) | |
| No | 105 (95%) | 64 (96%) | 41 (95%) | 1.00 |
| Age at Primary Cancer Diagnosis (years) | | | | |
| Mean (SD) | 8.3 (6) | 8.0 (6) | 8.6 (6) | 0.50 |
| Median (range) | 7.3 (0-20.7) | 6.7 (0-20.7) | 8.8 (0-20.6) | 0.36 |
| Age at Cardiomyopathy (years) | | | | |
| Mean (SD) | 17.6 (9) | 18.5 (9) | 16.6 (10) | 0.19 |
| Median (range) | 16.6 (0.4-41.8) | 17.6 (1-41.6) | 15.4 (0.4-41.8) | 0.36 |
| Length of Follow-up (years) | | | | |
| Mean (SD) | 9.2 (9) | 10.4 (8) | 7.9 (9) | 0.06 |
| Median (range) | 7.0 (0.1-35.1) | 9.1 (0.1-35.1) | 3.9 (0.1-30.3) | 0.01 |
| Within 1 year from primary dx | 32 (19%) | 11 (12%) | 21 (26%) | 0.02 |
| >=1 year from primary dx | 138 (81%) | 79 (88%) | 59 (74%) | |
| Year of Primary Diagnosis | | | | |
| 1966-1980 | 20 (12%) | 10 (11%) | 10 (13%) | |
| 1981-1990 | 41 (24%) | 20 (22%) | 21 (26%) | |
| 1991-2000 | 68 (40%) | 46 (51%) | 22 (27%) | |
| 2001-2008 | 41 (24%) | 14 (16%) | 27 (34%) | 0.009 |
| Year of Diagnosis of Cardiomyopathy | | | | |
| 1984-1990 | 4 (2%) | 1 (1%) | 3 (4%) | |
| 1991-2000 | 47 (28%) | 22 (25%) | 25 (31%) | |
| 2001-2005 | 72 (42%) | 38 (42%) | 34 (43%) | 0.35* |

Figure 4 (cont'd)

| Variables | Overall (n=170) | Asymptomatic (n=90) | Symptomatic (n=80) | P value |
|---|---|---|---|---|
| 2006-2008 | 47 (28%) | 29 (32%) | 18 (23%) | |
| Race/ Ethnicity | | | | |
| Non-Hispanic whites | 124 (73%) | 69 (77%) | 55 (69%) | |
| Hispanics | 16 (9%) | 8 (9%) | 8 (10%) | |
| Blacks | 12 (7%) | 5 (5%) | 7 (9%) | 0.68* |
| Other | 18 (11%) | 8 (9%) | 10 (12%) | |
| Cumulative Anthracycline Exposure (mg/m²) | | | | |
| Mean (SD) | 291 (142) | 279 (135) | 304 (149) | 0.26 |
| Median (range) | 300 (0-575) | 300 (0-480) | 330 (0-575) | 0.19 |
| 0 | 15 (9%) | 7 (8%) | 8 (10%) | |
| 1-100 | 7 (4%) | 5 (6%) | 2 (3%) | |
| 101-150 | 7 (4%) | 5 (6%) | 2 (3%) | |
| 151-200 | 9 (5%) | 6 (7%) | 3 (4%) | |
| 201-250 | 18 (11%) | 8 (9%) | 10 (12%) | |
| 251-300 | 33 (19%) | 20 (22%) | 13 (16%) | |
| >300 | 81 (48%) | 39 (43%) | 42 (52%) | 0.59 |
| Primary Diagnosis | | | | |
| Hodgkin lymphoma | 19 (11%) | 6 (7%) | 13 (16%) | |
| Non-Hodgkin lymphoma | 21 (12%) | 12 (13%) | 9 (11%) | |
| Bone tumor | 35 (21%) | 20 (22%) | 15 (19%) | |
| Soft tissue sarcoma | 20 (12%) | 13 (14%) | 7 (9%) | 0.02 |
| Acute lymphoblastic leukemia | 23 (14%) | 15 (17%) | 8 (10%) | |
| Acute myeloid leukemia | 19 (11%) | 4 (5%) | 15 (19%) | |
| Other | 33 (19%) | 20 (22%) | 13 (16%) | |
| Gender | | | | |
| Female | 94 (55%) | 43 (48%) | 51 (64%) | 0.04 |
| Chest Radiation | | | | |
| Yes | 43 (25%) | 21 (24%) | 21 (27%) | 0.66 |
| CBR1 1096G>A genotype | | | | |
| A/A | 2 (1%) | 2 (2%) | 0 (0%) | |
| G/A | 36 (21%) | 20 (22%) | 16 (20%) | |
| G/G | 132 (78%) | 68 (76%) | 64 (80%) | 0.51* |
| CBR3 V244M genotype | | | | |
| A/A | 21 (13%) | 12 (14%) | 9 (11%) | |
| G/A | 70 (41%) | 35 (39%) | 35 (44%) | |
| G/G | 78 (46%) | 42 (47%) | 36 (45%) | 0.81 |
| Combined CBR1 and CBR3 | | | | |
| Either G/A or A/A | 105 (62%) | 54 (61%) | 51 (64%) | |
| Both G/G | 64 (38%) | 35 (39%) | 29 (36%) | 0.68 |

* Exact test p value
[1] 35 cases do not have EF.
[2] 27 cases do not have SF.
[3] 2 cases with missing smoking status.
[4] 2 cases with unknown chest radiation.

[5] 1 case with unknown CBR3

Figure 6

| Cumulative Anthracycline exposure | CBR3 genotype status | Cases/Controls | Risk of cardiomyopathy for all patients* | | | |
|---|---|---|---|---|---|---|
| | | | OR (95%CI) | p-value | | |
| No exposure | CBR3:GA/AA | 9/56 | 1.0 | | Risk of cardiomyopathy stratified by anthracycline exposure(1-250mg/m², >250mg/m²)  | |
| | CBR3:GG | 6/36 | 0.86 (0.22-3.39) | 0.83 | OR (95% CI) | p-value |
| 1-250 mg/m² | CBR3:GA/AA | 15/84 | 1.66 (0.49-5.69) | 0.42 | 1.0 | |
| | CBR3:GG | 26/54 | 5.48 (1.81-16.63) | 0.003 | 3.30 (1.41-7.73) | 0.006 |
| 251+ mg/m² | CBR3:GA/AA | 67/51 | 18.92 (6.13-58.45) | <0.001 | 1.0 | |
| | CBR3:GG | 46/31 | 25.91 (7.67-87.57) | <0.001 | 1.37 (0.66-2.84) | 0.40 |

Odds ratios were obtained from conditional logistic regression adjusting for age at diagnosis, gender, and chest radiation.

*Reference group: no anthracycline exposure, CBR3:GA/AA genotype

**Reference group: CBR3:GA/AA genotype for the corresponding anthracycline exposure level

Figure 7

| Cumulative Anthracycline exposure | CBR1 genotype status | Cases/ Controls | Risk of cardiomyopathy for all patients* | | | | |
|---|---|---|---|---|---|---|---|
| | | | OR (95%CI) | p-value | | | |
| No exposure | CBR1:GA/AA | 7/23 | 1.0 | | Risk of cardiomyopathy stratified by anthracycline exposure (1-250mg/m²; >250mg/m²)** | | |
| | CBR1:GG | 8/68 | 0.35 (0.08-1.54) | 0.16 | OR (95% CI) | p-value | |
| 1-250 mg/m² | CBR1:GA/AA | 4/30 | 0.68 (0.13-3.59) | 0.65 | 1.0 | | |
| | CBR1:GG | 37/108 | 2.25 (0.62-8.21) | 0.22 | 3.29 (1.0-10.97) | 0.05 | |
| 251+ mg/m² | CBR1:GA/AA | 27/13 | 24.61 (5.4-112) | <0.001 | 1.0 | | |
| | CBR1:GG | 87/70 | 11.17 (2.9-12.59) | <0.001 | 0.45 (0.19-1.09) | 0.08 | |
| Odds ratios were obtained from conditional logistic regression adjusting for age at diagnosis, gender, and chest radiation. *Reference group: no anthracycline exposure and CBR1:GA/AA genotype  **Reference group: CBR1:GA/AA genotype for the corresponding anthracycline exposure level | | | | | | | |

Figure 8

| Cumulative Anthracycline exposure | CBR genotype status | Cases/ Controls | Risk of cardiomyopathy for all patients* | | Risk of cardiomyopathy stratified by anthracycline exposure(1-250mg/m$^2$; >250mg/m$^2$)** | |
|---|---|---|---|---|---|---|
| | | | OR (95%CI) | p-value | | |
| No exposure | CBR1:GA/AA-CBR3:GA/AA | 11/63 | 1.0 | | | |
| | | | | | OR (95% CI) | p-value |
| | CBR1:GG-CBR3:GG | 4/28 | 0.53 (0.10-2.67) | 0.44 | | |
| 1-250 mg/m$^2$ | CBR1:GA/AA-CBR3:GA/AA | 16/93 | 1.51 (0.47-4.81) | 0.49 | 1.0 | |
| | CBR1:GG-CBR3:GG | 25/43 | 5.39 (1.79-16.17) | 0.003 | 3.58 (1.54-8.29) | 0.04 |
| 251+ mg/m$^2$ | CBR1:GA/AA-CBR3:GA/AA | 78/55 | 17.40 (5.91-51.22) | <0.001 | 1.0 | |
| | CBR1:GG-CBR3:GG | 35/27 | 17.94 (5.64-57.08) | <0.001 | 1.03 (0.52-2.04) | 0.46 |

Odds ratios were obtained from conditional logistic regression adjusting for age at diagnosis, gender, and chest radiation.
*Reference group: no anthracycline exposure, CBR1:GA/AA genotype
**Reference group: CBR1:GA/AA-CBR3:GA/AA genotype for the corresponding anthracycline exposure level

Figure 9

|  | CBR3 genotype status | Cases/Controls | OR (95%CI) | p |
|---|---|---|---|---|
| No exposure | CBR1 GA/AA (referent group) | 7/23 | 1.0 | |
| | CBR1 GG | 8/66 | 0.36 (0.08-1.63) | 0.19 |
| 1-100 mg/m² | CBR1 GA/AA | 1/9 | 0.72 (0.07-7.98) | 0.79 |
| | CBR1 GG | 6/39 | 0.85 (0.18-4.10) | 0.84 |
| 101-150 mg/m² | CBR1 GA/AA | 1/6 | 1.59 (0.13-20.27) | 0.73 |
| | CBR1 GG | 6/29 | 2.44 (0.46-13.04) | 0.30 |
| 151-200 mg/m² | CBR1 GA/AA | 1/6 | 0.99 (0.07-13.61) | 0.99 |
| | CBR1 GG | 6/18 | 2.34 (0.44-12.40) | 0.32 |
| 201-250 mg/m² | CBR1 GA/AA | 1/7 | 0.36 (0.03-5.13) | 0.45 |
| | CBR1 GG | 17/22 | 5.46 (1.23-24.13) | 0.03 |
| 251-300 mg/m² | CBR1 GA/AA | 7/1 | 57.98 (4.60-731.22) | <0.001 |
| | CBR1 GG | 26/18 | 10.39 (2.39-45.11) | <0.001 |
| 301+ mg/m² | CBR1 GA/AA | 20/12 | 23.54 (4.71-117.69) | <0.001 |
| | CBR1 GG | 81/52 | 12.97 (3.08-54.60) | <0.001 |
| Odds ratios were obtained using conditional logistic regression adjusting for age at diagnosis, gender, and chest radiation. | | | | |

Figure 10

|  | CBR3 genotype status | Cases/Controls | OR (95%CI) | p |
|---|---|---|---|---|
| No exposure | CBR3:GA/AA (referent group) | 9/56 | 1.0 | |
| | CBR3:GG | 6/36 | 0.82 (0.20-3.38) | 0.79 |
| 1-100 mg/m² | CBR3:GA/AA | 3/30 | 0.78 (0.14-4.27) | 0.77 |
| | CBR3:GG | 4/17 | 2.16 (0.47-10.05) | 0.33 |
| 101-150 mg/m² | CBR3:GA/AA | 2/20 | 1.63 (0.25-10.63) | 0.61 |
| | CBR3:GG | 6/19 | 6.15 (1.32-28.70) | 0.02 |
| 151-200 mg/m² | CBR3:GA/AA | 3/17 | 1.75 (0.32-9.45) | 0.52 |
| | CBR3:GG | 6/7 | 6.37 (1.03-39.48) | 0.05 |
| 201-250 mg/m² | CBR3:GA/AA | 7/17 | 3.12 (0.68-14.78) | 0.15 |
| | CBR3:GG | 11/12 | 10.85 (2.72-43.17) | 0.00 |
| 251-300 mg/m² | CBR3:GA/AA | 18/11 | 14.95 (3.60-82.11) | 0.00 |
| | CBR3:GG | 15/8 | 24.99 (5.46-114.65) | <.0001 |
| 301+ mg/m² | CBR3:GA/AA | 49/40 | 21.93 (6.54-73.55) | <.0001 |
| | CBR3:GG | 31/23 | 27.71 (7.42-103.44) | <.0001 |
| Odds ratios were obtained using conditional logistic regression adjusting for age at diagnosis, gender, and chest radiation. | | | | |

Figure 11

| | CBR genotype status | Cases/Controls | OR (95%CI) | p |
|---|---|---|---|---|
| No exposure | CBR1:GA/AA-CBR3:GA/AA (referent group) | 11/63 | 1.0 | |
| | CBR1:GG-CBR3:GG | 4/28 | 0.48 (0.09-2.56) | 0.39 |
| 1-100 mg/m² | CBR1:GA/AA-CBR3:GA/AA | 4/32 | 0.89 (0.20-4.07) | 0.88 |
| | CBR1:GG-CBR3:GG | 3/15 | 1.48 (0.28-7.90) | 0.65 |
| 101-150 mg/m² | CBR1:GA/AA-CBR3:GA/AA | 2/25 | 1.18 (0.18-7.53) | 0.86 |
| | CBR1:GG-CBR3:GG | 5/12 | 8.54 (1.70-42.91) | 0.01 |
| 151-200 mg/m² | CBR1:GA/AA-CBR3:GA/AA | 3/16 | 1.60 (0.31-8.33) | 0.58 |
| | CBR1:GG-CBR3:GG | 6/7 | 6.11 (0.98-38.19) | 0.053 |
| 201-250 mg/m² | CBR1:GA/AA-CBR3:GA/AA | 7/28 | 2.83 (0.62-12.80) | 0.18 |
| | CBR1:GG-CBR3:GG | 11/9 | 12.10 (2.91-50.40) | <0.001 |
| 251-300 mg/m² | CBR1:GA/AA-CBR3:GA/AA | 22/11 | 16.28 (4.19-63.15) | <0.001 |
| | CBR1:GG-CBR3:GG | 11/8 | 12.67 (3.06-52.56) | <0.001 |
| 301+ mg/m² | CBR1:GA/AA-CBR3:GA/AA | 58/44 | 19.14 (5.97-61.31) | <0.001 |
| | CBR1:GG-CBR3:GG | 24/19 | 21.66 (5.97-78.64) | <0.001 |
| Odds ratios were obtained using conditional logistic regression adjusting for age at diagnosis, gender, and chest radiation. | | | | |

US 9,650,678 B2

METHODS FOR IDENTIFYING AN INCREASED RISK OF ANTHRACYCLINE-RELATED CARDIOTOXICITY

CROSS-REFERENCE TO RELATED APPLICATIONS

This application claims the benefit of U.S. Provisional Patent Application No. 61/734,778, filed Dec. 7, 2012, which is incorporated herein by reference in its entirety.

STATEMENT OF GOVERNMENT INTEREST

The present invention was made with government support under Grant No. U01 GM073646, awarded by the NIH/NIGMS Pharmacogenomics Research Network; and Grant No. U10 CA98543, awarded by the National Cancer Institute. The Government has certain rights in the invention.

BACKGROUND

Anthracyclines are one of the most effective classes of drugs currently available for cancer diagnosed across the entire age spectrum. However, the therapeutic potential of anthracyclines is limited because of their strong dose-dependent relation with progressive and irreversible cardiomyopathy leading to congestive heart failure (Blanco et al., 2012; Grenier et al., 1998; Barry et al., 2008). This dose-dependent risk is modified by younger age at anthracycline exposure, chest radiation and co-existence of cardiovascular disease risk factors, such as hypertension and diabetes (Puma et al., 2008; Armenian et al., 2011). However, a significant inter-individual variability exists; cumulative anthracycline exposure as low as 150 mg/m$^2$ results in cardiomyopathy in some patients, while exposure as high as 1000 mg/m$^2$ is tolerated without cardiomyopathy by others (Bryant et al., 2007).

Thus, it would be beneficial to determine the reasons for the observed inter-individual variability and develop an optimal anthracycline dosage regimen for cancer patients based on the risk of developing cardiotoxicity from the effects of these drugs.

SUMMARY

In one embodiment, methods of identifying a subject, for example, a cancer patient, having an increased risk of developing anthracycline-related cardiotoxicity are provided. Such methods may include isolating a DNA sample from a biological specimen from the subject; genotyping the DNA sample to determine a copy number of a variant allele that increases the risk of developing chemotherapy-induced cardiotoxicity; and identifying the subject as having an increased risk of developing anthracycline-related cardiotoxicity when the copy number is at least one.

In some embodiments, the methods may include optimally administering a therapeutically effective dose of a chemotherapy agent or an alternative non-cardiotoxic chemotherapeutic agent to the subject. The optimal administration of the chemotherapy agent prevents or minimizes the agent's toxic effects, yet does not compromise its ability to effectively treat primary cancer. In some aspects, the variant allele comprises a single nucleotide polymorphism (SNP). The SNP may be part of an HAS3 or a CBR gene, for example, rs2232228(G>A), or CBR3V244M. In some aspects, the chemotherapy agent is an anthracycline. In other aspects, the chemotherapy-induced cardiotoxicity prevented is cardiomyopathy or congestive heart failure (CHF).

BRIEF DESCRIPTION OF THE DRAWINGS

FIG. 1 is a table providing the demographic/therapeutic characteristics and risk of cardiomyopathy.

FIG. 2 is a table providing the CBR1 and CBR3 genotypes and risk of cardiomyopathy.

FIG. 3 provides the demographic and clinical characteristics of the study population. Abbreviations: SD, standard deviation. *Matching variables. Because of variation in the number of controls per patient case, the percentage of controls and patient cases in each category of a specific matching variable may not be identical. †Five patients with unknown chest radiation were excluded. ‡Nine patients with noninformative genotypes were excluded. §Exact P value. ||Summation of rows Both AA/GA; CBR1 GG and CBR3 AA/GA; CBR1 AA/GA and CBR3 GG; and Both GG.

FIG. 4 is a table providing clinical and demographic characteristics of the cardiomyopathy cases by type.

FIG. 6 provides data illustrating the CBR1 and CBR3 genotypes and risk of cardiomyopathy.

FIG. 7 illustrates the modifying effect of CBR1 genotypes on dose-dependent risk of anthracycline-related cardiomyopathy.

FIG. 8 illustrates the modifying effect of CBR1 and CBR3 genotypes on dose-dependent risk of anthracycline-related cardiomyopathy.

FIG. 9 shows the data for the CBR1 genotype and dose-dependent risk of anthracycline-related cardiomyopathy.

FIG. 10 shows the data for the CBR3 genotype and dose-dependent risk of anthracycline-related cardiomyopathy.

FIG. 11 shows the data for the CBR1 and/or CBR3 genotypes and dose-dependent risk of anthracycline-related cardiomyopathy.

DETAILED DESCRIPTION

Figure 5:
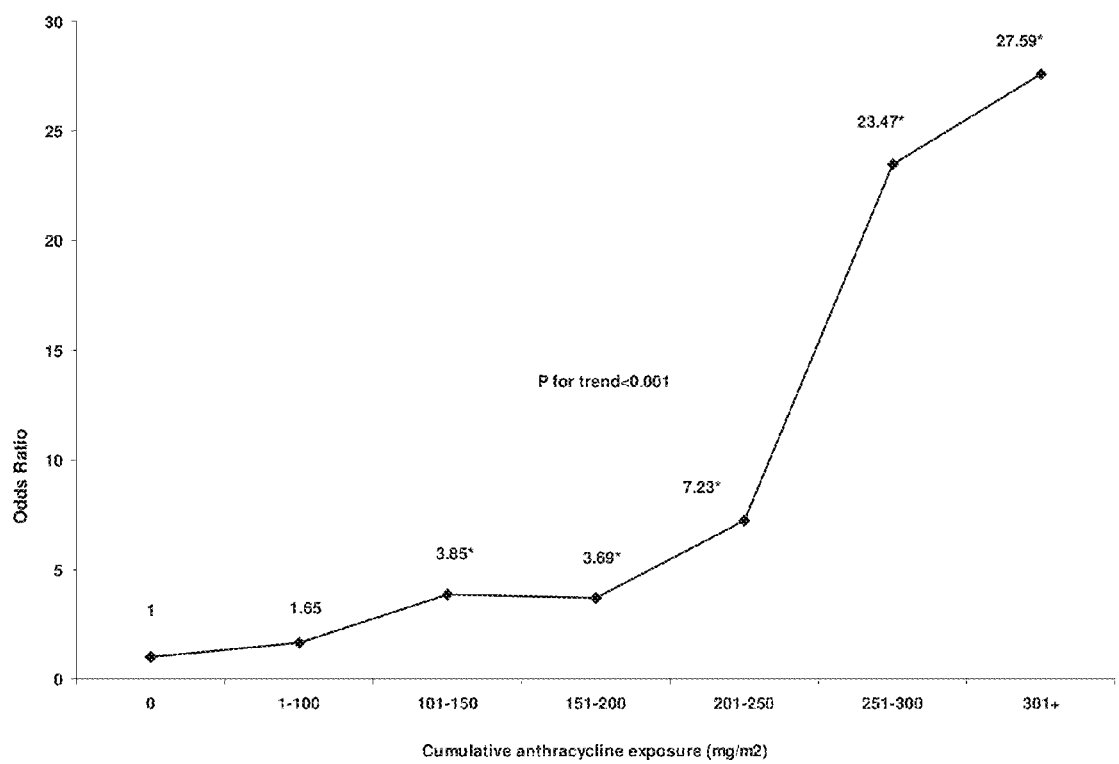
FIG. 5 illustrates the dose-response relationship between cumulative anthracycline exposure and risk of cardiomyopathy. Patients with no exposure to anthracyclines served as the referent group. Magnitude of risk is expressed as odds ratio, which was obtained using conditional logistic regression adjusting for age at diagnosis, gender, and chest radiation.

Methods of identifying a subject (e.g., cancer patients) having an increased risk of developing anthracycline-related cardiotoxicity and methods for preventing or reducing said risk as a result of treating a cancer patient with a chemotherapeutic agent are provided herein. Such methods are based on identifying the subject's genotype or the number of copies of a variant allele carried by the subject.

According to certain embodiments described herein, a method of identifying a subject having an increased risk of developing anthracycline-related cardiotoxicity may include isolating a DNA sample from a biological specimen from the subject using a suitable method known in the art and genotyping the DNA sample.

The genotype may be determined based on the number of copies of a variant allele carried by a cancer patient. A subject is determined to have an increased risk of developing anthracycline-related cardiotoxicity when the copy number is at least one. The method may optionally include administering a chemotherapeutic agent based on the patient's genotype.

The methods described herein may also be used to prevent or reduce the risk of any type of acute or delayed cardiotoxic events that are common to patients treated with chemotherapeutic agents including, but not limited to, myocarditis, and cardiomyopathy, which is indicated by a reduction in left ventricular ejection fraction (LVEF), signs and symptoms of congestive heart failure (e.g., tachycardia, dyspnea, pulmonary edema, dependent edema, cardiomegaly, hepatomegaly, oliguria, ascites, pleural effusion, and arrhythmias).

Chemotherapeutic agents that may cause cardiotoxic events may include, but are not limited to, alkylating agents, antimetabolites, anti-tumor antibiotics (e.g., Anthracyclines), topoisomerase inhibitors, mitotic inhibitors hormone therapy, targeted therapeutics and immunotherapeutics. In certain embodiments, anthracyclines may be responsible for causing cardiomyopathy and other cardiotoxic events when administered as a cancer therapy, and may be optimally administered alone or in combination with one or more additional chemotherapeutic agents according to the embodiments described herein. Examples of anthracyclines that may be administered according to the embodiments described herein include, but are not limited to, doxorubicin, daunomycin, epirubicin, mitoxantrone, valrubicin, and idarubicin. A strong dose-dependent association between anthracyclines and cardiomyopathy limits the therapeutic potential of this effective class of therapeutic agents, suggesting that identification of those at highest risk is important so that anthracycline exposure may be tailored to maximize the efficacy of these drugs.

The methods described herein may be used to prevent cardiotoxicity during the treatment of any type of cancer including, but not limited to, bone cancer, bladder cancer, brain cancer, neuroblastoma, breast cancer, cancer of the urinary tract, carcinoma, cervical cancer, childhood cancers (e.g., astrocytoma, brain stem glioma, NCS atypical teratoid/rhabdoid tumor, CNS embryonal tumor, CNS Germ Cell tumors, craniopharyngioma, ependymoma, kidney tumors, acute lymphoblastic leukemia, acute myeloid leukemia, and other types of leukemia; Hodgkin lymphoma, non-Hodgkin lymphoma, Ewing sarcoma, osteosarcoma and malignant fibrous histiocytoma of the bone, rhabdomyosarcoma, soft tissue sarcoma, and Wilms' tumor,), colon cancer, esophageal cancer, gastric cancer, head and neck cancer, hepatocellular cancer, liver cancer, lung cancer, lymphoma and leukemia, melanoma, ovarian cancer, pancreatic cancer, pituitary cancer, prostate cancer, rectal cancer, renal cancer, sarcoma, stomach cancer, testicular cancer, thyroid cancer, uterine cancer.

In some embodiments, the methods described herein may include a step of determining the genotype ("genotyping") (e.g., heterozygous for an allele (XA or XG), or homozygous for an allele (AA or GG)) of an isolated DNA sample to determine the number of copies (or "a copy number") of a variant allele that increases a cancer patient's risk of developing chemotherapy induced cardiotoxicity. The copy number may be determined by any suitable whole genome or locus-specific method known in the art including, but not limited to microarray methods, SNP-array methods, fluorescence in situ hybridization (FISH), restriction fragment length polymorphism (RFLP) followed by Southern blot, quantitative real-time PCR, locus specific PCR, multiplex ligation-dependent probe amplification (MLPA), competitive fluorescent multiplex STRP assay (CFMSA), pyrosequencing, ligation detection reaction, and the invader assay. Such methods may also be used to screen for any variant alleles that are associated with chemotherapy-induced cardiotoxicity.

The copy number may be determined using a DNA sample obtained from a cancer patient. The DNA sample may be derived from any biological specimen containing DNA including, but not limited to, any material, biological fluid, tissue, or cell obtained or otherwise derived from the cancer patient including, but not limited to, blood (including whole blood, leukocytes, peripheral blood mononuclear cells, buffy coat), and saliva. This also includes experimentally separated fractions of all of the preceding. For example, a blood sample can be fractionated into fractions containing particular types of blood cells, such as red blood cells or white blood cells (leukocytes). If desired, a sample may be a combination of samples from an individual, such as a combination of a tissue and fluid sample. A biological specimen may also include materials containing homogenized solid material, such as from a stool sample, a tissue sample, or a tissue biopsy; or materials derived from a tissue culture or a cell culture.

As discussed above, there is significant inter-individual variability related to the development of chemotherapy-induced cardiotoxicity. The Examples described below investigate the reason(s) for this observed inter-individual variability by identifying single nucleotide polymorphisms (SNPs) that might modify the association between anthracycline exposure and risk of cardiotoxicity. The ITMAT/Broad CARe (IBC) cardiovascular SNP-array was used that profiles SNPs in 2100 genes considered relevant for cardiovascular disease in the general population (Keating et al., 2008). A 2-stage design was used that included a discovery and a replication stage. In the discovery stage, both the main effects of SNPs as well as gene-environment (anthracycline) interactions were examined. SNPs surpassing a pre-specified threshold for statistical significance were validated in the replication stage using an independent set of cases with anthracycline-related cardiomyopathy.

Thus, in some embodiments, the allele may include a mutation, deletion or single nucleotide polymorphism (SNP). In some embodiments, the SNP is part of a gene associated with cardiotherapeutic agent metabolism, or cardiovascular conditions or diseases, including, but not limited to, genes in the HAS or CBR families. For example, the SNP may be an A allele on SNP rs2232228 (rs2232228(G>A)), or CBR3 V244M, which are described further below.

In some embodiments, the variant allele that increases the risk of developing cardiotoxic effects is part of a gene associated with cardiovascular condition or disease. In one embodiment, the variant allele is part of the family of hyaluronan synthase genes (e.g., HAS3), including, but not limited to, a variant allele that includes an SNP, such as rs2232228. The HAS3 gene, located on chromosome 16, encodes for an enzyme that produces hyaluronan (HA). HA is a ubiquitous component of extracellular matrix (ECM) (Spicer et al., 2004), and plays a dynamic role in organization of ECM following injury or inflammation by providing a matrix to support cellular migration and adhesion (Spicer et al., 2004; Jiang et al., 2005; Laurent et al., 1992; Knudson et al., 1993; Toole et al., 1990; West et al., 1985; Zhang et al., 2000). HA is especially enriched in matrices undergoing remodeling. HAS3 has been implicated in organ dysfunction, such as ventilator-related lung injury (Jacobson et al., 2000; McKee et al., 1996; Noble et al., 1996; Bourguignon et al., 2011; Bai et al., 2005) and phosphodiesterase-3 inhibitor reduces inflammatory effects by directly inhibiting HAS3 expression (Mrabat et al., 2009).

In the myocardium, ECM provides a scaffold for alignment of myocytes, fibroblasts, endothelial cells and vasculature (Gorda et al., 2000). In myocardial infarction, with consequent apoptosis of myocytes, cardiac fibroblasts serve as a central mediator of cardiac remodeling, using the ECM as a scaffold (Burlew et al., 2000). HA accumulates after myocardial infarction in rats (Waldenstrom et al., 1991), and HA synthesis is part of the extensive remodeling seen in cardiac hypertrophy (Hellman et al., 2008). Anthracyclines injure heart muscle through induction of apoptosis in myocytes, which is then followed by replacement fibrosis (Perik et al., 2005). Anthracycline-related cardiotoxicity is directly linked to the amount of anthracyclines in the heart (Meissner et al., 2002; Begg et al., 1994). ECM is likely involved in cardiac remodeling (from inflammation to fibrosis) after anthracycline-related injury; the extent of remodeling and repair is possibly modulated by variability in HA production in the ECM, consistent with the genotype-dependent cardiomyopathy risk observed in the current study. Thus, high-dose anthracyclines likely trigger differential expression/HA synthesis based on the genotype of rs2232228, influencing cardiac remodeling.

As described in the Examples below, a two-stage design was used to determine host susceptibility to anthracycline-related cardiomyopathy. The ITMAT/Broad CARe cardiovascular SNP-array was used to profile common single nucleotide polymorphisms (SNPs) in 2100 genes considered most relevant to de novo cardiovascular disease. In this matched case-control design (93 cases, 194 controls), a common SNP rs2232228 was identified in the hyaluronan synthase (HAS3) gene that exerts a substantial modifying effect on anthracycline dose-dependent risk of cardiomyopathy. Among individuals with rs2232228 GG genotype, cumulative anthracycline exposure was not associated with cardiomypathy risk at any dose. On the other hand, in individuals with AA genotype, cardiomypathy risk increased substantially with increasing anthracycline exposure; individuals exposed to high-dose (>250 mg/m$^2$) anthracyclines, the presence of rs2232228 AA genotypes were at 8.5-fold (95% CI, 2.0-35.6, p=0.004) increased cardiomyopathy risk, compared with GG genotype. The gene-environment interaction between SNP rs2232228 and high-dose anthracycline exposure was replicated in an independent set of 76 patients with anthracycline-related cardiomyopathy. The significant modifying effect of HAS3 genotype on the dose-dependent association between anthracycline and cardiomyopathy risk suggests that genotyping HAS3 may help to tailor anthracycline exposure to maximize benefit.

In other embodiments, the variant allele that increases the risk of developing cardiotoxic effects is part of a gene involved with anthracycline metabolism. The main route for anthracycline metabolism is a two-electron reduction of the C-13 carbonyl group in the anthracycline side chain, resulting in the formation of alcohol metabolites (erg, doxorubicinol, daunorubicinol) (Mordente et al., 2009; Minotti et al., 2004). Development of cardiomyopathy correlates with myocardial accumulation of anthracycline alcohol metabolites (Mushlin et al., 1993; Stewart et al., 1993). Variability in the formation of these metabolites could influence the risk of cardiomyopathy (Mordente et al., 2009). Synthesis of cardiotoxic alcohol metabolites is catalyzed by myocardial cytosolic carbonyl reductases (CBRs) (Mordente et al., 2009; Kalabus et al., 2010). In humans, two monomeric CBRs (CBR1 and CBR3) are encoded for by genes located on chromosome 21. Single nucleotide polymorphisms (SNPs) in the 3'-untranslated regions of CBR1 where nucleotide 1096, a guanine (G), is replaced by adenine (A) (CBR1 1096G>A); and in CBR3 where amino acid 244, a valine (V), is replaced by methionine (M) (CBR3V244M), impacts catalytic activity for anthracycline substrates (Bains et al., 2010; Gonzalez-Covarrubias et al., 2009; Lakhman et al., 2005). The goal of the current study was to understand the contribution of functional polymorphisms in CBR1 and CBR3 to the dose-dependent risk of anthracycline-related cardiomyopathy in survivors of childhood cancer.

As described in detail in Example 1 below, one hundred seventy survivors with cardiomyopathy (patient cases) were compared with 317 survivors with no cardiomyopathy (controls; matched on cancer diagnosis, year of diagnosis, length of follow-up, and race/ethnicity) using conditional logistic regression techniques. A dose-dependent association was observed between cumulative anthracycline exposure and cardiomyopathy risk (0 mg/m$^2$: reference; 1 to 100 mg/m$^2$: odds ratio [OR], 1.65; 101 to 150 mg/m$^2$: OR, 3.85; 151 to 200 mg/m$^2$: OR, 3.69; 201 to 250 mg/m$^2$: OR, 7.23; 251 to 300 mg/m$^2$: OR, 23.47; >300 mg/m2: OR, 27.59; $P_{trend}$<0.001). Among individuals carrying the variant A allele (CBR1:GA/AA and/or CBR3:GA/AA), exposure to low- to moderate-dose anthracyclines (1 to 250 mg/m$^2$) did not increase the risk of cardiomyopathy. Among individuals with CBR3 V244M homozygous G genotypes (CBR3:GG), exposure to low- to moderate-dose anthracyclines increased cardiomyopathy risk when compared with individuals with CBR3:GA/AA genotypes unexposed to anthracyclines (OR, 5.48; P=0.003), as well as exposed to low- to moderate-dose anthracyclines (OR, 3.30; P=0.006). High-dose anthracyclines (>250 mg/m2) were associated with increased cardiomyopathy risk, irrespective of CBR genotype status.

This study demonstrated that an increased anthracycline-related cardiomyopathy risk exists at doses as low as 101 to 150 mg/m$^2$. Homozygosis for G allele in CBR3 contributes to increased cardiomyopathy risk associated with low- to moderate-dose anthracyclines, such that there seems to be no safe dose for patients homozygous for the CBR3 V244M G allele. These results, along with those regarding the rs2232228(G>A) allele within HAS3, suggest a need for targeted intervention for those at increased risk of cardiomyopathy.

Thus, according to some embodiments, the methods described herein may include a step of optimally administering a therapeutically effective dose of a chemotherapeutic agent based on a cancer patient's genotype. The genotype may be measured as a copy number as determined above. The optimal administration addresses the need for targeted intervention for patients with an increased risk of cardiotoxicity who are also receiving a chemotherapeutic treatment. Alternatively, in some embodiments where a patient has been identified as having in increased risk of anthracycline induced cardiotoxicity, the methods may include a step of administering a non-cardiotoxic chemotherapeutic, cardioprotective agent or treatment, in lieu of an anthracycline or other chemotherapeutic agent that may cause cardiotoxic events. Non-cardiotoxic chemotherapeutics, cardioprotective agents or treatments that may be used in accordance with the methods described herein may include those described below.

Cancer patients are typically administered a maximum safe dosage of a particular cancer treatment or combination treatment, including chemotherapeutics and targeted cancer therapies. A "maximum safe dosage," "maximum tolerated dosage" or "maximum recommended therapeutic dosage" is the highest amount of a therapeutic agent that can be given that minimizes complications or side effects to a patient while maintaining its efficacy as a treatment. Such a dose can be adjusted to consider the patient's overall heath and any extenuating factors that could hamper the patient's recovery. Due to the severity and potential lethal outcome of the cancer being treated, a maximum safe dosage tolerated in cancer treatment may be an amount that causes considerable and severe side effects, including cardiotoxic effects. In some embodiments, the maximum safe dosage is represented by a cumulative dose of the therapeutic agent, which is the total amount of the therapeutic agent given to a patient over the course of treatment. For example, anthracyclines such as doxorubicin are typically administered at a dosage of 60-75 mg/m$^2$ every three to four weeks when administered as a single agent and 25-60 mg/m$^2$ every three to four weeks when administered in combination with one or more additional chemotherapeutic agents. However, according to the package insert for doxorubicin hydrochloride injection (Teva Parenteral Medicines, Inc.), the risk of developing cardiotoxicity that manifests as potentially fatal congestive heart failure (CHF) increases rapidly with increasing total cumulative doses of doxorubicin in excess of 400 mg/m$^2$. Thus, in some embodiments, the maximum safe dosage may be approximately 400-500 mg/m$^2$ or any suitable dosage greater than 400 mg/m$^2$, based on factors related to each individual patient's disease state.

A "therapeutically effective amount," "optimally effective amount" "effective amount," "effective dose," or the like, is an amount of a therapeutic agent that produces a desired therapeutic effect in a subject, such as preventing or treating a target condition or alleviating symptoms associated with the condition. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005

In some embodiments, a therapeutically effective dose of a particular agent may be a cumulative dosage that is the same as or lower than a maximum effective dose. A therapeutically effective dose for a particular agent used in accordance with the embodiments described herein may be a low cumulative dose (or a "low dose") ranging from about 1-150 mg/m$^2$, a moderate cumulative dose (or a "moderate dose") ranging from about 151-250 mg/m$^2$, a low-to-moderate cumulative dose (or a "low-to-moderate dose") that is less than 250 mg/m$^2$ or ranging from about 1-250 mg/m$^2$, or a high cumulative dose (or a "high dose"), which includes doses greater than 250 mg/m$^2$. In some embodiments, the therapeutically effective dose may be a cumulative dose that is approximately 1-100 mg/m$^2$, approximately 101-150 mg/m$^2$, approximately 151-200 mg/m$^2$, approximately 201-250 mg/m$^2$, approximately 251-300 mg/m$^2$, approximately 301-350 mg/m$^2$, approximately 351-400 mg/m$^2$, approximately 401-500 mg/m$^2$, less than approximately 250 mg/m$^2$, over approximately 250 mg/m$^2$, or any suitable dosage greater than 400 mg/m$^2$, based on factors related to each individual patient's disease state.

Each individual patient's dosage may be tailored to the patient's needs based on their genotype or copy number. In some embodiments, the therapeutically effective dose that is administered to a cancer patient includes a low to moderate cumulative dose of a chemotherapeutic agent (e.g., anthracycline) when the patient carries at least one copy of the variant allele that increases the risk of developing cardiotoxic effects (e.g., rs2232228(G>A) or CBR3 V244M). In some aspects, the low to moderate cumulative dose is less than 250 mg/m$^2$ or between approximately 1-250 mg/m$^2$ when the patient carries at least one copy of the variant allele. In such embodiments, the patient may be heterozygous (carries one copy of the variant allele) or homozygous (carries two copies of the variant allele) for the variant allele that increases the risk of developing cardiotoxic effects.

In other embodiments, the therapeutically effective dose that is administered to a cancer patient includes a low cumulative dose of a chemotherapeutic agent (e.g., anthracycline) when the patient carries two copies of the variant allele that increases the risk of developing cardiotoxic effects (e.g., rs2232228(G>A) or CBR3 V244M). In some aspects, the low cumulative dose is less than 150 mg/m$^2$ or between approximately 1-100 mg/m$^2$, between approximately 101-150 mg/m$^2$, or between approximately 1-150 mg/m$^2$ when the patient carries two copies of the variant allele. In such embodiments, the patient is homozygous (carries two copies of the variant allele) for the variant allele that increases the risk of developing cardiotoxic effects.

The therapeutically effective dose may include one or more doses of the chemotherapeutic agent (e.g., anthracycline) administered at regular intervals. Standard chemotherapy is typically administered by an intravenous infusion once every three to four weeks (i.e., intervals of approximately 21-28 days), but may be administered at any suitable interval that results in effective treatment of a malignancy.

In some embodiments, the optimal therapeutically effective dose of the chemotherapeutic agent may be administered in combination with one or more additional chemotherapeutic or cardioprotective agents or treatments or in combination with one or more chemotherapeutic regimens known in the field of oncology. "In combination" or "in combination with," as used herein, means in the course of treating the same disease in the same patient using two or more agents, drugs, treatment regimens, treatment modalities or a combination thereof, in any order. This includes simultaneous administration, as well as in a temporally spaced order of up to several days apart. Such combination treatment may also include more than a single administration of any one or more of the agents, drugs, treatment regimens or treatment modalities. Further, the administration of the two or more agents, drugs, treatment regimens, treatment modalities or a combination thereof may be by the same or different routes of administration.

Examples of cardioprotective agents or treatments that may be used in accordance with the methods described herein include, but are not limited to, cardioprotective drugs (e.g., dexrazoxane, ACE-inhibitors, diuretics, cardiac glycosides) cholesterol lowering drugs, revascularization drugs, anti-inflammatory drugs, cardioprotective diets, cardioprotective nutrients, cardioprotective herbs, cardioprotective vitamins (e.g., folic acid, B vitamin family), and cardioprotective hormone treatments.

Examples of targeted therapies that may be used in accordance with the methods described herein include, but are not limited to, selective estrogen receptor modulators (SERMs) (e.g., tamoxifen, toremifene and fulvestrant), aromatase inhibitors (anastrozole, exemestane and letrozole), kinase inhibitors (imatinib mesulate, dasatinib, nilotinib, lapatinib, gefitinib, erlotinib, temsirolimus and everolimus), growth factor receptor inhibitors (e.g., Trastuzumab, cetuximab and panitumumab), regulators of gene expression (vorinostat, romidepsin, bexarotene, alitretinoin and tretinoin), apoptosis inducers (bortezomib and pralatrezate), angiogenesis inhibitors (bevacizumab, sorafenib, sunitinib and pazopanib), antibodies that trigger a specific immune response by binding a cell-surface protein on lymphocytes (rituximab, alemtuzumab and ofatumumab), antibodies or other molecules that deliver toxic molecules specifically to cancer cells (tositumomab, ibritumomab tiuxetan, denileukin diftitox), cancer vaccines and gene therapy.

Examples of additional chemotherapeutic agents that may be used in accordance with the methods described herein include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, bacillus calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, interferon alpha, interleukin-2, interleukin-4, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, or zoledronic acid.

Examples of known chemotherapeutic regimens may include, but are not limited to, ABVD, AC, BEACOPP, BEP, CA (or AC), CAF, CAV, CBV, ChIVPP/EVA, CHOP (or COHP), R-CHOP, COP (or CVP), CMF, COPP, EC, ECF, EP, EPOCH, FEC, FL (also known as Mayo), FOLFOX, FOLFIRI, ICE, ICE-R, m-BACOD, MACOP-B, MOPP, PCV, ProMACE-MOPP, ProMACE-CytaBOM, R-FCM, Stanford V, Thal/Dex, TIP, VAC, VAD, VAPEC-B, and VIP. Further explanation of these chemotherapeutic regimens is found in Table 1 below.

TABLE 1

Chemotherapeutic Regimens.

| Regimen | Components |
| --- | --- |
| ABVD | Adriamycin (doxorubicin), bleomycin, vinblastine, dacarbazine |
| AC | Adriamycin (doxorubicin), cyclophosphamide |
| BEACOPP | Bleomycin, etoposide, Adriamycin (doxorubicin), cyclophosphamide, Oncovin (vincristine), procarbazine, prednisone |
| BEP | Bleomycin, etoposide, platinum agent (cisplatin) |
| CA | Cyclophosphamide, Adriamycin (doxorubicin) (same as AC) |
| CAF | Cyclophosphamide, Adriamycin (doxorubicin), fluorouracil (5-FU) |

TABLE 1-continued

Chemotherapeutic Regimens.

| Regimen | Components |
|---|---|
| CAV | Cyclophosphamide, Adriamycin (doxorubicin), vincristine |
| CBV | Cyclophosphamide, BCNU (carmustine), VP-16 (etoposide) |
| ChlVPP/EVA | Chlorambucil, vincristine (Oncovin), procarbazine, prednisone, etoposide, vinblastine, Adriamycin (doxorubicin) |
| CHOP or COHP | Cyclophosphamide, hydroxydoxorubicin (doxorubicin), vincristine (Oncovin), prednisone |
| CHOP-R or R-CHOP | CHOP + rituximab |
| COP or CVP | Cyclophosphamide, Oncovin (vincristine), prednisone |
| CMF | Cyclophosphamide, methotrexate, fluorouracil (5-FU) |
| COPP | Cyclophosphamide, Oncovin (vincristine), procarbazine, prednisone |
| EC | Epirubicin, cyclophosphamide |
| ECF | Epirubicin, cisplatin, fluorouracil (5-FU) |
| EP | Etoposide, platinum agent (cisplatin) |
| EPOCH | Etoposide, prednisone, Oncovin, cyclophosphamide, and hydroxydaunorubicin |
| FEC | Fluorouracil (5-FU), epirubicin, cyclophosphamide |
| FL (Also known as Mayo) | Fluorouracil (5-FU), leucovorin (folinic acid) |
| FOLFOX | Fluorouracil (5-FU), leucovorin (folinic acid), oxaliplatin |
| FOLFIRI | Fluorouracil (5-FU), leucovorin (folinic acid), irinotecan |
| ICE | ifosfamide, carboplatin, etoposide (VP-16) |
| ICE-R | ICE + rituximab |
| m-BACOD | Methotrexate, bleomycin, Adriamycin (doxorubicin), cyclophosphamide, Oncovin (vincristine), dexamethasone |
| MACOP-B | Methotrexate, leucovorin (folinic acid), Adriamycin (doxorubicin), cyclophosphamide, Oncovin (vincristine), prednisone, bleomycin |
| MOPP | Mechlorethamine, Oncovin (vincristine), procarbazine, prednisone |
| PCV | Procarbazine, CCNU (lomustine), vincristine |
| ProMACE-MOPP | Methotrexate, Adriamycin (doxorubicin), cyclophosphamide, etoposide + MOPP |
| ProMACE-CytaBOM | Prednisone, doxorubicin (adriamycin), cyclophosphamide, etoposide, cytarabine, bleomycin, Oncovin (vincristine), methotrexate, leucovorin |
| R-FCM | Rituximab, fludarabine, cyclophosphamide, mitoxantrone |
| Stanford V | Doxorubicin, mechlorethamine, bleomycin, vinblastine, vincristine, etoposide, prednisone |
| Thal/Dex | Thalidomide, dexamethasone |
| TIP | Paclitaxel, ifosfamide, platinum agent cisplatin |
| VAC | Vincristine, Actinomycin, Cyclophosphamide |
| VAD | Vincristine, Adriamycin (doxorubicin), dexamethasone |
| VAPEC-B | Vincristine, Adriamycin (doxorubicin), prednisone, etoposide, cyclophosphamide, bleomycin |
| VIP | Etoposide, ifosfamide, platinum agent cisplatin |

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1

Anthracycline-Related Cardiomyopathy after Childhood Cancer: Role of Polymorphisms in Carbonyl Reductase Genes Patients and Methods
  Study Design.
  Children's Oncology Group (COG) ALTE03N1 is a case-control study aimed at understanding the pathogenesis of cardiomyopathy in childhood cancer survivors. One hundred twenty-one COG member institutions contributed patients to the study after obtaining approval from local institutional review boards. Written informed consent/assent was obtained from all patients and/or their parents/legal guardians.
  Participants.
  Prevalent cases and matched controls were identified from patients diagnosed with a primary cancer at age 21 years or younger and followed at a COG institution. Cases consisted of individuals who developed cardiomyopathy after completion of cancer therapy and were alive at study participation. For each case, one to four controls were randomly selected from childhood cancer survivors without cardiomyopathy, using the following matching criteria: 1) cancer diagnosis; 2) year of diagnosis (±5 years); 3) race/ethnicity; and 4) duration of follow-up for controls to exceed time from cancer diagnosis to cardiomyopathy for index case. All participants provided a biologic specimen (blood [85%]; buccal cells/saliva [15%]). One hundred and seventy cases with cardiomyopathy and 317 matched controls participated in this study.
  Cancer Therapy.
  Detailed information regarding therapeutic exposures was abstracted from medical records. Total anthracycline exposure was calculated by multiplying the cumulative dose/m$^2$ of individual anthracyclines (doxorubicin, daunomycin, epirubicin, and idarubicin) by a factor that reflects the drug's cardiotoxic potential (Table 2) (Lehmann et al., 2000) and then summing the result.

TABLE 2

Calculation of Cumulative Anthracycline Exposure

| Name of Anthracycline | Conversion factor to Doxorubicin Isotoxic Dose |
|---|---|
| Doxorubicin | 1 |
| Daunomycin | 0.833 (⅚) |
| Idarubicin | 5 |
| Epirubicin | 0.67 (⅔) |

Cumulative anthracycline exposure was treated as a categorical variable. Radiation therapy with heart in the radiation field was designated as "chest radiation" and summarized as a yes/no variable.

Validation of Cardiomyopathy.

All anthracycline-exposed individuals had normal cardiac function prior to anthracycline initiation. Clinical and echocardiographic documentation of cardiomyopathy was provided by participating sites. Cases were considered eligible if they fulfilled the American Heart Association (AHA) criteria for cardiac compromise by presenting with symptoms (dyspnea, orthopnea, fatigue, etc.) and/or signs (edema, hepatomegaly, rales, etc.) of cardiac decompensation or, in the absence of symptoms/signs, had echocardiographic features of left ventricular dysfunction as evidenced by ejection fraction (EF)≤40% and/or fractional shortening (SF)≤28%.

Controls had no symptoms or signs of cardiac compromise (all 317 controls) and had normal echocardiographic features (n=203; EF: median=65 [range, 53-84]; SF: median=36 [range, 29-61]) or no clinical indication for echocardiographic examination because of lack of exposure to anthracyclines or chest radiation (n=63). In addition, echocardiograms were unavailable for 51 anthracycline-exposed (n=41) or chest radiation-exposed (n=10) controls. Thus, echocardiograms were unavailable for 114 controls. Exclusion of these 114 controls did not materially alter the associations (FIGS. 1 and 2); therefore, the 114 controls were included in the analysis.

DNA Isolation and Genotyping.

Genomic DNA was isolated from peripheral blood or buccal cells/saliva by using QIAamp or Qiagen kits (Qiagen, Valencia, Calif.) and Puregene (Qiagen) or Oragene (DNA Genotek, Kanata, Ontario, Canada) kits, respectively. The CBR3 V244M and CBR1 1096G>A polymorphisms (rs1056892, rs9024) were analyzed using validated assays for allelic discrimination with specific fluorescent probes (Applied Biosystems, Foster City, Calif.) (Gonzalez-Covarrubias et al., 2009; Lakhman et al., 2005). Laboratory personnel were blinded to case-control status. Nine samples had noninformative results.

Statistical Analysis.

Univariate conditional logistic regression and generalized linear models were used to compare cases and controls for categorical and continuous characteristics, respectively. Chi-square tests were used to test for deviation from Hardy-Weinberg equilibrium.

Anthracycline Exposure and Cardiomyopathy.

Association between anthracycline exposure and cardiomyopathy was measured by estimating the odds ratio (OR) while controlling for chest radiation (yes/no), age at cancer diagnosis (continuous variable in years), and gender, using conditional logistic regression techniques. Cumulative anthracycline exposure was categorized as 0 mg/m$^2$, 1-100 mg/m$^2$, 101-150 mg/m$^2$, 151-200 mg/m$^2$, 201-250 mg/m$^2$, 251-300 mg/m$^2$, and >300 mg/m$^2$.

CBR Genes and Cardiomyopathy.

SNPs in CBR1 and CBR3 genes were examined individually and in combination. For the combined analysis, patients homozygous for both the CBR1 and CBR3G allele (i.e., CBR1:GG and CBR3:GG [associated with increased CBR activity]) served as the group of interest, while patients carrying at least one copy of the variant A allele in either of the CBR genes (i.e., CBR1:GA/AA and/or CBR3:GA/AA) served as the reference group. Conditional logistic regression was used to adjust for cumulative anthracycline exposure in addition to gender, age at cancer diagnosis, and chest radiation.

Modifying Effect of CBR Genes on Dose-Dependent Risk of Anthracycline Related Cardiomyopathy.

The interactive effect of genes and anthracycline exposure was examined by including genotypes (CBR1 and CBR3 individually as well as in combination), anthracycline exposure, and the product of CBR genotypes and anthracycline exposure in the model. The risk of cardiomyopathy was examined at varying levels of anthracycline exposure (no exposure: 0 mg/m$^2$; low to moderate dose: 1-250 mg/m$^2$; and high dose: >250 mg/m$^2$) for the two risk categories of the CBR genotypes (homozygosis for GG v GA/AA), using CBR GA/AA genotype and no exposure to anthracyclines as the referent group. Next, the modifying effect of the CBR genotypes was examined by stratifying on the dose categories of anthracyclines.

Data were analyzed using SAS 9.2 (SAS Institute, Cary, N.C.). All statistical tests were two-sided; p values<0.05 were considered statistically significant. Bonferroni adjustment was used for multiple comparisons (0.05/2=0.025) when analyzing the association with the two SNPs.

Results

Demographic/Clinical Characteristics and Risk of Cardiomyopathy.

Demographic and clinical characteristics of the 170 cases and 317 matched controls are summarized in FIG. 3. Median EF and SF for the cases was 42% (range, 10% to 68%) and 24% (5% to 33%), respectively. One hundred and sixty-six cases (98%) met the echocardiographic cut offs for cardiomyopathy (EF 40% and/or SF 28%); the remaining four cases presented with signs/symptoms of cardiac compromise per American Heart Association guidelines, despite echocardiographic values exceeding the cut offs. Echocardiographic and clinical details of the cases are summarized in FIG. 4 and Table 3. Cases had been treated for bone tumor/soft tissue sarcoma (33%), acute leukemia (25%), lymphoma (23%), and other diagnoses (19%). Cases were more likely to have received chest radiation (25% v 14%, p<0.001) and anthracyclines (91% v 71%, p<0.001), as well as higher cumulative doses of anthracyclines (mean, 291 v 168 mg/m$^2$, p<0.001). The association between demographic and clinical characteristics and risk of cardiomyopathy is detailed in FIG. 1.

TABLE 3

Prevalence of symptoms and signs of cardiac dysfunction per AHA criteria.

| AHA Criteria | Prevalence | Fractional shortening median (range) | Ejection fraction median (range) |
|---|---|---|---|
| Symptoms | | | |
| Dyspnea/orthopnea | 52 (65%) | 20 (5-28) | 35 (10-52) |
| Fatigue | 36 (45%) | 21 (5-33) | 40 (13-57) |

TABLE 3-continued

Prevalence of symptoms and signs of cardiac dysfunction per AHA criteria.

| AHA Criteria | Prevalence | Fractional shortening median (range) | Ejection fraction median (range) |
|---|---|---|---|
| Signs | | | |
| Edema | 31 (39%) | 17 (5-27) | 35 (10-53) |
| Hepatomegaly | 13 (16%) | 20 (9-27) | 33 (21-59) |
| Rales | 14 (18%) | 17 (9-27) | 33 (15-52) |
| Any symptom or sign | 80 (100%) | 20 (5-33) | 36 (10-59) |

Anthracycline Dose.

After adjusting for age at diagnosis of cancer, gender, and chest radiation, there was a clear dose-dependent association between anthracycline exposure and cardiomyopathy risk. Compared with patients without anthracycline exposure, the risk of cardiomyopathy increased with each dose category (1-100 mg/m$^2$: OR=1.65, 101-150 mg/m$^2$: OR=3.85, 151-200 mg/m$^2$: OR=3.69, 201-250 mg/m$^2$: OR=7.23, 251-300 mg/m$^2$: OR=23.47, and >300 mg/m$^2$: OR=27.59, respectively, p for trend <0.001, FIG. 5.

Other Risk Factors.

Chest radiation was associated with an increase in risk of cardiomyopathy (OR=4.29; 95% CI, 1.9 to 9.6; p<0.001). However, female gender (OR=1.47, 95% CI, 0.9 to 2.4, p=0.13) and older age at cancer diagnosis (OR=0.99/yr, 95% CI, 0.93-1.04; p=0.59) were not associated with cardiomyopathy risk.

Polymorphisms in Carbonyl Reductase Genes and Cardiomyopathy.

CBR1 1096G>A and CBR3 V244M genotype distributions were consistent with those predicted under conditions of Hardy-Weinberg equilibrium (CBR1 1096G>A: p=0.79; CBR3 V244M: p=0.27) and were similar to those previously reported (p>0.05) (Gonzalez-Covarrubias et al., 2009; Lakhman et al., 2005) (FIG. 3). As shown in FIG. 2, there was no association between CBR1 genotype status and cardiomyopathy risk. On the other hand, the risk of cardiomyopathy was higher for individuals with homozygous CBR3 GG genotype relative to those carrying at least one copy of the variant CBR3 A allele (OR=1.79; p=0.02; FIG. 2). Combined analysis of CBR1 and CBR3 genotype status revealed a non significant increase in cardiomyopathy risk for individuals with CBR1:GG-CBR3:GG genotypes (OR=1.53; p=0.09; FIG. 2).

Modifying Effect of Polymorphisms in Carbonyl Reductase Genes and Dose-Dependent Risk of Anthracycline-Related Cardiomyopathy.

The modifying effect of CBR genotype status on the dose-dependent association between anthracyclines and risk of cardiomyopathy was analyzed for CBR1, CBR3, and the CBR1-CBR3 combination.

CBR1 1096G>A:

For individuals with CBR1:GA/AA genotypes exposed to low- to moderate-dose anthracyclines (1-250 mg/m$^2$), the risk of cardiomyopathy was not statistically significantly different from the risk in individuals with CBR1:GA/AA not exposed to anthracyclines (OR=0.68, p=0.65, FIG. 7). Individuals with CBR1:GG genotype exposed to low to moderate doses of anthracyclines showed a non significant increase in the risk for cardiomyopathy when compared to individuals with CBR1:GA/AA genotypes not exposed to anthracyclines (OR=2.25, p=0.22, FIG. 7). Within the low- to moderate-dose category, the CBR1:GG genotype was associated with a nonsignificantly increased risk of cardiomyopathy when compared to the CBR1:GA/AA genotypes (OR=3.29, p=0.05, FIG. 7). Further adjustment for CBR3 genotype attenuated the association (OR=2.63, p=0.11). CBR1:GG genotype was not associated with increased risk of cardiomyopathy within the high-dose category (FIG. 7).

CBR3 V244M:

For individuals with CBR3:GA/AA genotype exposed to low- to moderate-dose anthracyclines (1-250 mg/m$^2$), the risk of cardiomyopathy was not statistically significantly different from individuals with CBR3:GA/AA genotype with no anthracycline exposure (OR=1.66, p=0.42, FIG. 6). However, individuals with CBR3:GG genotype exposed to low- to moderate-dose anthracyclines were at increased risk of cardiomyopathy when compared to subjects with CBR3:GA/AA genotypes not exposed to anthracycline (OR=5.48, p=0.003, FIG. 6). Within the low-to moderate-dose category, CBR3:GG genotype status was associated with an increased risk of cardiomyopathy when compared to the CBR3:GA/AA genotypes (OR=3.30; p=0.006, FIG. 6). Further adjustment for CBR1 genotype did not change the association (OR=3.48; p=0.005, FIG. 6). CBR3:GG genotype was not associated with cardiomyopathy within the high-dose category.

CBR1 and/or CBR3:

The modifying effect of the combined CBR1 and CBR3 genotypes on the dose dependent association between anthracyclines and cardiomyopathy risk was similar to that observed for the CBR3 genotype (FIG. 8).

Figure 12:
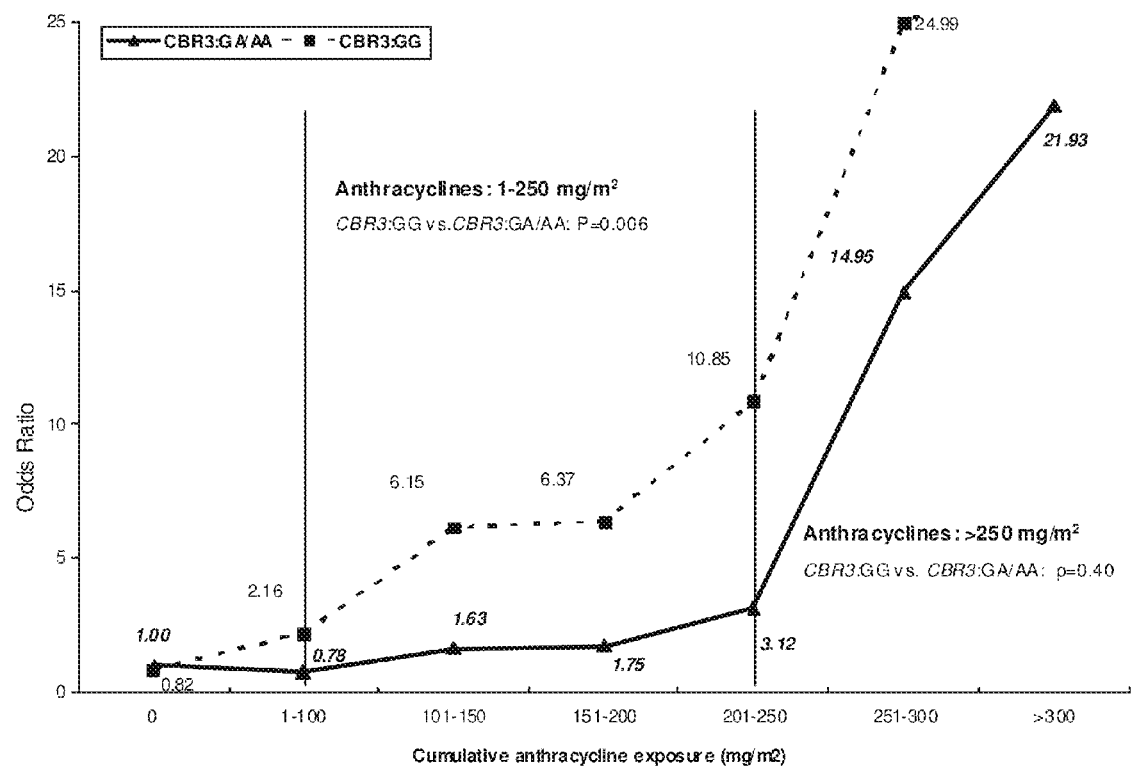
FIG. 12 illustrates the dose-response relationship between cumulative anthracycline exposure and risk of cardiomyopathy stratified by patients' CBR3 genotype status (CBR3: GG and CBR3:GA/AA). Patients with no exposure to anthracyclines and carrying CBR3:GA/AA genotype served as the referent group. Magnitude of risk is expressed as Odds Ratio, which was obtained using conditional logistic regression adjusting for age at diagnosis, gender, and chest radiation.

Next, the dose-response relation between anthracycline exposure and cardiomyopathy was examined, stratified by the patients' CBR genotype status (patients carrying at least one copy of the variant A allele vs. those homozygous for the G allele; FIGS. 9-11). These results indicate that homozygosis for the G allele in CBR3 gene was primarily responsible for modifying the risk for cardiomyopathy. As shown in FIG. 12, among patients with at least one copy of the A allele in CBR3, low- to moderate-dose anthracycline exposure was not associated with cardiomyopathy when compared with patients not exposed to anthracyclines. On the other hand, among patients homozygous for the G allele in CBR3, low-dose anthracycline exposure was associated with an increased risk of cardiomyopathy (101-150 mg/m$^2$: OR=6.15; 95% CI, 1.3-28.8; p=0.02; 151-200 mg/m$^2$: OR=6.37; 95% CI, 1.0-39.5; p=0.05; and 201-250 mg/m$^2$: OR=10.85; 95% CI, 2.7-43.2; p<0.001) when compared with patients with at least one copy of the variant A allele in CBR3 and no exposure to anthracyclines. In contrast, doses exceeding 250 mg/m$^2$ were associated with an increased risk of cardiomyopathy, irrespective of patients' CBR3 genotype status.

Erosion of Disease Risk Effect Size Due to Survival Bias.

The presence of survival bias risks under-ascertainment of genotypes associated with high lethality, with consequent underestimation of disease risk effect sizes for those genotypes associated with both increased disease risk and disease-associated lethality (Hernan et al., 2004). As described herein, genetic variants have been identified that simultaneously confer modest risk of disease and substantial risk of lethality, which could affect the results in case-control genetic association studies. Tools that allow calculation of effect size erosion caused by survival bias have been developed. Anderson et al. have developed a formula to allow estimation of effect size erosion given a variant's odds ratio of disease, odds ratio of lethality, and minor allele frequencies (MAF) (Anderson et al., 2011). Thus, using the variant's MAF, genotype relative-risk of disease (GRR-D), and genotype relative risk of lethality (GRR-L) in addition to disease annual incidence (Φ) and disease-related mortality (φ) estimates for the age range of included subjects, the percent erosion of effect size is calculated as described below:

$$\% \text{ effect size erosion} = \exp(8.73(\Theta) \times 1.4(\Phi) + 0.067(\text{GRR-D}) + 1.02(\text{MAF}) + 1.53(\text{GRR-L}) - 7.25)$$

Using this formula, the degree of erosion of the true estimate due to survival bias in this case-control study was estimated. In order to do this, the MAF for CBR1 to be 0.2 and for CBR3 to be 0.4 was used; and an estimated incidence rate of cardiomyopathy of 0.003 per year from a cohort of children treated with anthracycline in the Netherlands was used (van Dalen et al., 2006). The following assumptions were then made: i) a fairly high mortality rate of 50%; ii) a (GRR-D) of 2 and (GRR-L) also of 2. Using these assumptions, the maximum possible effect size erosion was only about 2.7%. However, if the GRR-L was assumed to be 3 (i.e., the high-risk genotype is associated with a 3-fold increased risk of death), the maximum possible effect size erosion could be 12%.

Discussion

Anthracyclines play an undisputed role in the treatment of childhood cancer (Granowetter et al., 2009; Grier et al., 2003; Johnson et al., 1998); unfortunately, development of dose-dependent cardiomyopathy limits their therapeutic potential (Gianni et al., 2008). An elevated risk of clinical heart failure was reported by 5-F year survivors of childhood cancer exposed to anthracycline doses exceeding 250 mg/m$^2$ (Mulrooney et al., 2009). The current study demonstrates elevated risk of clinically validated cardiomyopathy at lower doses, such that patients exposed to a cumulative dose of 101-150 mg/m$^2$ are at increased risk compared to the unexposed (OR=3.9). The current study also demonstrates that at low to moderate doses of anthracycline exposure, individual differences in anthracycline pharmacodynamics modify the risk of cardiomyopathy.

Myocardial accumulation of anthracycline alcohol metabolites influences the course of cardiomyopathy (Mushlin et al., 1993; Stewart et al., 1993). These metabolites form a reservoir in the cardiomyocytes and impair contractility through inhibition of Ca$^{2+}$ and Na$^+$/K$^+$ pump activity (Mushlin et al., 1993; Boucek et al., 1987; Olson et al., 1998). In the human heart, CBRs are considered major anthracycline-metabolizing enzymes (Mordente et al., 2009; Mordente et al., 2003). Functional polymorphisms in CBR1 and CBR3 modulate the synthesis of anthracycline alcohol metabolites. The rate of doxorubicinol synthesis is 1.5-fold higher in liver samples with CBR1 1096G>A homozygous G genotype compared with samples with heterozygous G/A genotype (Gonzalez-Covarrubias et al., 2009). CBR3 V244M polymorphism results in CBR3 protein isoforms (CBR3 V244, CBR3M244) with distinct catalytic properties (Bains et al., 2010; Lakhman et al., 2005); CBR3 V244 (G allele) catalyzes the synthesis of doxorubicinol 2.6 times faster than CBR3M244 (A allele) (Blanco et al., 2008).

The current study examined the modifying effect of CBR11066G>A and CBR3 V244M genotype status on the dose dependent risk of anthracycline-related cardiomyopathy. Among individuals carrying at least one copy of the variant A allele in CBR1 and/or CBR3, low- to moderate-dose anthracycline exposure (1-250 mg/m$^2$) was not associated with cardiomyopathy. The risk of cardiomyopathy, however, was significantly increased among individuals with CBR3:GG genotype exposed to low- to moderate-dose anthracycline exposure when compared to unexposed individuals carrying at least one copy of the A allele. On the other hand, the risk of cardiomyopathy was modest and statistically non significant for individuals with CBR1:GG genotype exposed to low- to moderate-dose anthracyclines. CBR1 or CBR3 genotype status did not impact cardiomyopathy risk among those exposed to high-dose anthracyclines.

Homozygosis for the G allele in CBR3 gene appears to drive the increase in risk for cardiomyopathy associated with low- to moderate dose anthracyclines. The differential impact of CBR1 and CBR3 genotype status on cardiotoxicity may be explained, in part, by recent findings on the bases that control the transcription of both genes (Ebert et al., 2010; Zhang et al., 2009; Lakhman et al., 2007). CBR3 expression is modulated by the master transcription factor Nrf2 (nuclear factor [erythroid-derived 2]-like 2, NFE2L2), whereas expression of CBR1 appears to be predominantly regulated through the aryl hydrocarbon receptor pathway (AHR) (Ebert et al., 2010; Lakhman et al., 2007). Nrf2 coordinates the induction of a battery of genes involved in protection against oxidative stress. Here, it is proposed that the Nrf2 pathway provides a link between the acute cardiotoxicity mediated mostly by reactive oxidative species (ROS) and chronic cardiotoxicity induced by anthracycline C-13 alcohol metabolites. Parent anthracyclines induce ROS production and Nrf2 translocation into the nucleus. In turn, nuclear Nrf2 upregulates CBR3 expression with consequent increase in synthesis of cardiotoxic anthracycline alcohol metabolites. This upregulation of CBR3 activity in a chronic setting may help explain why the association with cardiomyopathy appears to be stronger for polymorphic CBR3 than for polymorphic CBR1.

Restriction of the modifying effect of CBR genotype status only to low- to moderate-dose anthracyclines is intriguing. In humans, approximately 50% of anthracyclines remain unmetabolized (Joerger et al., 2005) and induce cardiotoxicity through mechanisms that invoke ROS production (Minotti et al., 2004; Menna et al., 2008). CBR activity contributes to the pathogenesis of cardiomyopathy by generation of cardiotoxic anthracycline alcohol metabolites, three possible scenarios could be envisaged, depending on the dose of anthracyclines. First, in the absence of anthracycline exposure, CBR activity does not play a role in the development of cardiomyopathy due to of lack of substrate. Second, exposure to low- to moderate-dose anthracyclines provides the necessary substrate to synthesize cardiotoxic C-13 alcohol metabolites by the high-risk/high-activity CBR variants, resulting in an increased risk of cardiomyopathy. Finally, in the presence of high-dose anthracyclines, cardiotoxicity is mostly mediated by the oxidative stress generated by the excess of unmetabolized anthracyclines, such that anthracycline alcohol metabolites play a relatively minor role. However, it is also possible that cardiomyopathy in individuals exposed to high-dose anthracyclines and carrying the high-risk variants (CBR1:GG-CBR3:GG) is associated with high lethality, thus removing these individuals from the pool of eligible cases and reducing the association in this group to null.

Prevalent case-control studies by the very nature of their design exclude fatal endpoints from the case set. Presence of survival bias risks under-ascertainment of genotypes associated with high lethality, with consequent underestimation of disease risk effect size for those genotypes associated with both increased disease risk and disease-associated lethality (Hernan et al., 2004). Using the methodology developed by Anderson et al (Anderson et al., 2011) to estimate effect size erosion, the maximum possible degree of erosion of the true estimate as a result of survival bias in this case-control study was calculated to be 12%, assuming that the high-risk genotype was associated with a three-fold increased risk of death (see Results section).

Furthermore, in order for early cardiac death to have eliminated the association from an anticipated genotype-outcome risk of 3.0 to 1.0 (i.e., associated with a 67% erosion) due to an overrepresentation of the GG genotype among those who had received high-dose anthracyclines and died prior to study participation, the high-risk genotype would need to be associated with a four-fold increased risk of death when compared with the low-risk genotype. There is no data to support such a high level of lethality. However, since it is logistically impossible to prove this within the context of a large multi-institutional study, it is acknowledged that the possibility among recipients of high-dose anthracyclines, patients with CBR1:GG-CBR3:GG genotype, could have been more likely to have developed cardiomyopathy and died, thus becoming lost from the sampling frame and eroding the true association between high-risk variants and cardiomyopathy.

Here, it is recognized that interindividual variability in alternate metabolic pathways, such as reduction to semiquinone radicals by a number of oxidoreductases or two-electron reduction by aldo keto reductases, and in pharmacodynamic targets (e.g., calsequestrin, iron regulatory proteins) could play a role in modulating cardiomyopathy risk (Joerger et al., 2005). However, functional, biochemical and genetic studies support CBR-mediated reduction of anthracyclines to cardiotoxic alcohol metabolites as a major metabolic route implicated in the pathogenesis of cardiotoxicity (Forrest et al., 2000; Olson et al., 2003). Furthermore, findings in this study confirmed the association between CBR3 V244M genotype and cardiomyopathy reported in a small previously published study (Blanco et al., 2008). The current study demonstrates that patients with CBR3 V244M homozygous G genotype exposed to low- to moderate-dose anthracyclines are at an increased risk of cardiomyopathy, even at cumulative exposures between 101 and 150 mg/m$^2$. These results could allow for enhanced surveillance and/or prevention strategies among childhood cancer survivors at increased risk of cardiomyopathy.

Example 2

Hyaluronidase Synthase 3 (HAS3) Variant and Anthracycline-Related Cardiomyopathy Materials and Methods
Study Participants
Discovery Set:

The discovery set was drawn from a Children's Oncology Group study (COG-ALTE03N1, PI: Bhatia) that aimed to understand the pathogenesis of cardiomyopathy in childhood cancer survivors. COG member institutions contributed patients after obtaining approval from local institutional review boards. Written informed consent/assent was obtained from patients/parents/legal guardians. Cases and controls were identified from individuals diagnosed with cancer at age ≤21 years. Cases consisted of individuals who developed cardiomyopathy after completion of cancer therapy, and were alive at study participation. For each case, 1 to 4 controls were randomly selected from the same COG childhood cancer survivor cohort, using the following matching criteria: 1) cancer diagnosis; 2) year of diagnosis (±5 years); 3) race/ethnicity; and 4) duration of cardiomyopathy-free follow-up for controls to exceed time from cancer diagnosis to cardiomyopathy for the corresponding case.

Four hundred and one individuals (130 cases; 271 controls) participated in this study. All participants provided a biological specimen (blood [89%], buccal cells/saliva [11%]) for DNA.

Anthracycline-exposed participants had normal cardiac function prior to initiation of anthracyclines. Cases fulfilled American Heart Association (AHA) criteria for cardiac compromise by presenting with symptoms (dyspnea, orthopnea, fatigue) and/or signs (edema, hepatomegaly, rales) of cardiac compromise, along with echocardiographic evidence of left ventricular dysfunction; or, in the absence of symptoms/signs, had echocardiographic features of left ventricular dysfunction (ejection fraction [EF]≤40')/0 and/or fractional shortening [SF]≤28%). Controls had no symptoms/signs of cardiac compromise coupled with normal echocardiographic features in the anthracycline-exposed individuals.

Replication Set:

An independent set of 76 patients diagnosed at City of Hope (COH) with cardiomyopathy following anthracycline exposure were drawn from the COH Long-term Follow-up study (IRB #00029), that follows patients undergoing hematopoietic cell transplantation (HCT) for the development of cardiomyopathy (Armenian et al., 2011). The protocol was approved by the COH institutional review board, and written informed consent/assent was obtained from patients/parents/legal guardians. Eligible cases fulfilled AHA criteria for cardiac compromise, along with echocardiographic confirmation of cardiac compromise.

Therapeutic Exposures

Total lifetime anthracycline exposure was calculated by multiplying the cumulative dose (mg/m$^2$) of individual anthracyclines (doxorubicin, daunomycin, epirubicin, idarubicin, mitoxantrone) by a factor that reflects the drug's cardiotoxic potential (Table S1, Shankar et al., 2008), and then summing the results. Radiation therapy with heart in the field was designated as "chest radiation". Total body irradiation at ≥12 Gy was included as chest radiation.

Genotyping and Quality Control
Discovery Set:

Genomic DNA was isolated from peripheral blood/buccal cells/saliva by using QIAamp/Qiagen kits and Puregene/Oragene kits, respectively. Genotyping was performed on the Illumina IBC cardiovascular SNP-array by the Center for Applied Genomics at The Children's Hospital of Philadelphia and the University of Pennsylvania. The IBC cardiovascular SNP-array includes a prioritized list of 2100 candidate genes potentially involved in cardiovascular diseases (Keating et al., 2008). This array uses a "cosmopolitan" approach to determine tagging SNPs for loci of interest to cover genetic diversity in populations of different ancestry (De Bakker et al., 2006).

Quality control (QC) for genotype data were performed with the PLINK toolset (Purcell et al., 2007). Of the 401 study participants, 399 (99.5%; 129 cases, 270 controls) met call rates >95%. No duplicated samples or sample contamination was identified. The Multidimensional Scaling method (Purcell et al., 2007) was used to cluster individuals into two sub-populations: non-Hispanic whites and "others". In order to control for potential population stratification, 112 individuals in the "other" category were filtered out, retaining 287 non-Hispanic whites (93 cases, 194 controls) in the discovery stage analysis. After adjusting for the overall genomic control inflation factor ($\lambda$=1.27), the type I error appeared to be under control. For the 287 individuals, the total genotyping rate exceeded 98.9%. Of the 43,293 autosomal SNPs in the IBC SNP-array, 988 that failed a missingness threshold for missing fraction >0.05, and 7,267 that failed a frequency threshold for a minor allele frequency (MAF)<0.01 were removed. A check for Hardy-Weinberg Equilibrium (HWE) resulted in exclusion of 108 SNPs with P value<0.000001. The final dataset included 34,912 autosomal SNPs.

Replication Set:

Genomic DNA was extracted from peripheral blood and buccal cells/saliva, using Qiagen kits. Genomic DNA from formalin fixed, paraffin-embedded bone marrow biopsies or from unstained slides of bone marrow smear was extracted using QuickExtract FFPE DNA Extraction Solution (Epicentre Biotechnologies, Madison, Wis.). Significant SNP(s) identified in the discovery stage were genotyped using Sequenom iPLEX SNP chemistry on a MassArray system (call rate=93.4%).

Statistical Analysis

Discovery Stage:

Discovery stage was designed as a genome-wide association study (GWAS) to examine both the main effects of SNPs as well as gene-environment (anthracycline) interactions. For each SNP that successfully passed the QC, MAF, and HWE filters, conditional logistic regression techniques were employed (Model 1) in R (see R. project):

$$\text{logit}(p) = \text{matched set} + \text{agedx} + \text{gender} + \text{RT} + \text{anthracycline} + \text{SNP} + \text{SNP}*\text{anthracycline} \quad (\text{Model 1})$$

p is the probability of cardiomyopathy in a subject conditional on matched set; SNP denotes genotype for each SNP in additive coding; anthracycline represents cumulative anthracycline dose in mg/m$^2$ (continuous variable); RT denotes chest radiation (yes/no); agedx denotes age at diagnosis of primary cancer (continuous variable)

Figure 15:
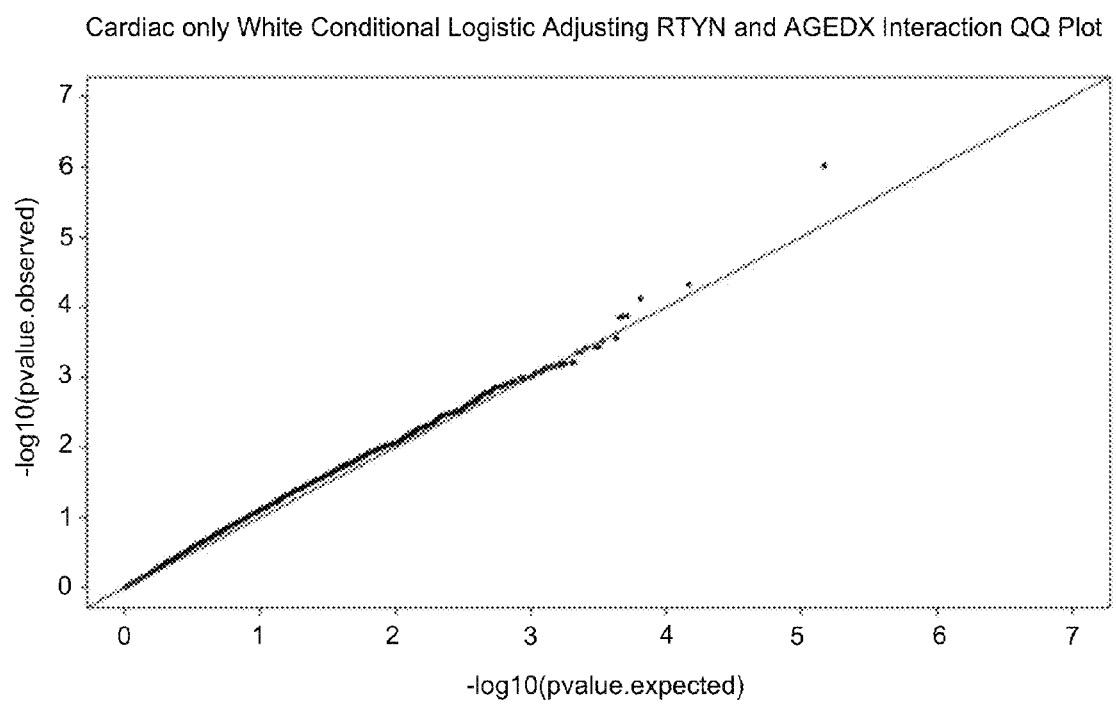
FIG. 15 displays the QQ plot for the p value of the gene environment (anthracycline) interaction (cardiac only white conditional logistic adjusting RTYN and AGEDX Interaction). Note, the type I error is under control and there is no obvious population stratification.

Taking into consideration linkage disequilibrium (LD) among SNPs and the QC results, it was estimated that ~10,000 tests were conducted as part of the genome-wide analysis. Therefore, a p value<5×10$^{-6}$ was selected as the threshold for the whole genome significance test, accounting for multiple testing (Cappola et al., 2010). The QQ plot for the p value of the gene environment (anthracycline) interaction indicates that there is no population stratification (FIG. 15). Odds ratio estimates were interpreted as approximate relative risk estimates because of the relative rarity of cardiomyopathy.

Replication Stage:

Replication stage used a case-only design to verify significant gene-environment interactions that were identified in the discovery stage. Cumulative anthracycline exposure was dichotomized as low-to-moderate-dose (1-250 mg/m$^2$) and high-dose (>250 mg/m$^2$), based on a significantly increased risk of cardiomyopathy associated with anthracycline exposure exceeding 250 mg/m$^2$ observed in recent studies (see above). Genotype distributions of significant SNPs in the high-dose anthracycline group were compared with those in the low-to-moderate-dose group. Treating the binary variable of anthracycline exposure as a dependent variable, logistic regression techniques were used to conduct a gene-environment interaction analysis shown in Model 2.

$$\text{logit}(p\_\text{anth}\_\text{exp}) = \text{agedx} + \text{gender} + \text{RT} + \text{race/ethnicity} + \text{SNP} \quad (\text{Model 2})$$

p_anth_exp is the probability of being in high-dose anthracycline exposure group; anth_exp 0 = low-to-moderate dose; 1 = high-dose Final Model.

Finally, using a case-only design, Model 2 was used to test gene-environment interactions for significant SNP(s) identified in discovery stage, using the combined data from the discovery and replication sets.

Results

Discovery Stage

Demographic/Clinical Characteristics.

Demographic and clinical characteristics of the cases and controls are summarized below in Table 4. Cases were more likely to have received a higher cumulative anthracycline exposure (median dose: 300 mg/m$^2$ vs. 152 mg/m$^2$, p<0.001) and chest radiation (24.7% vs. 11.3%, p=0.01). Among the cases, median EF was 40% (range, 10%-56%), and median SF was 23% (5%-33%); 99% of the cases met echocardiographic cut-offs for cardiomyopathy (EF 40% and/or SF 28%).

TABLE 4

Characteristics of the Study Population in the Discovery and Replication Sets

| Variable | Discovery Set | | | Replication Set |
|---|---|---|---|---|
| | Cases (n = 93) | Controls (n = 194) | P value | Cases (n = 76) |
| Race/ethnicity[1] | | | | |
| Non-Hispanic whites | 93 (100%) | 194 (100%) | Matched | 45 (59.2%) |
| Hispanics | 0 (0%) | 0 (0%) | | 21 (27.6%) |
| African Americans | 0 (0%) | 0 (0%) | | 3 (4.0%) |
| Asians | 0 (0%) | 0 (0%) | | 7 (9.2%) |
| Age at Primary Cancer Diagnosis (years) | | | | |
| Median (range) | 6.9 (0-20.2) | 6.3 (0-20.6) | 0.43 | 48 (13-68) |
| Age at Study Participation (years) | | | | |
| Median (range) | 19.4 (0.4-41.7) | 18.5 (3.5-49.2) | 0.35 | 55 (16-71) |
| Gender | | | | |
| Females | 53 (57.0%) | 100 (51.5%) | 0.74 | 44 (58%) |
| Primary Diagnosis[1] | | | | |
| Hodgkin lymphoma | 11 (11.8%) | 17 (8.8%) | Matched | 14 (18.4%) |
| Non-Hodgkin lymphoma | 11 (11.8%) | 15 (7.7%) | | 34 (47.4%) |
| Bone tumors | 22 (23.7%) | 32 (16.5%) | | 0 (0%) |

TABLE 4-continued

Characteristics of the Study Population in the Discovery and Replication Sets

| Variable | Discovery Set | | | Replication Set |
|---|---|---|---|---|
| | Cases (n = 93) | Controls (n = 194) | P value | Cases (n = 76) |
| Soft tissue sarcoma | 9 (9.7%) | 10 (5.2%) | | 0 (0%) |
| ALL | 12 (12.9%) | 62 (32.0%) | | 5 (6.6%) |
| AML | 8 (8.6%) | 20 (10.3%) | | 10 (13.2%) |
| Other | 20 (21.5%) | 38 (19.6%) | | 11 (14.5%) |
| Year of Primary Cancer Diagnosis[1] | | | | |
| 1966-1980 | 17 (18.2%) | 12 (6.2%) | Matched | 0 (0%) |
| 1981-1990 | 28 (30.1%) | 43 (22.2%) | | 9 (11.8%) |
| 1991-2000 | 33 (35.5%) | 97 (50.0%) | | 51 (67.1%) |
| 2001-2008 | 15 (16.1%) | 42 (21.7%) | | 16 (21.1%) |
| Length of Follow-up (years)[1] | | | | |
| Median (range) | 10.0 (0.1-35.1) | 11.3 (0.9-41.0) | 0.10 | 4.0 (0.5-22.5) |
| Cumulative Anthracycline Exposure (mg/m$^2$) | | | | |
| Median (range) | 300 (0-630) | 152 (0-825) | <0.0001 | 300 (60-649) |
| 0 mg/m$^2$** | 7 (7.5%) | 43 (22.2%) | | 0 (0%) |
| 1-100 mg/m$^2$ | 2 (2.2%) | 31 (16.0%) | | 1 (1.3%) |
| 101-150 mg/m$^2$ | 6 (6.5%) | 22 (11.3%) | | 8 (10.5%) |
| 151-200 mg/m$^2$ | 4 (4.3%) | 13 (6.7%) | | 6 (7.9%) |
| 201-250 mg/m$^2$ | 9 (9.7%) | 21 (10.8%) | | 12 (15.8%) |
| 251-300 mg/m$^2$ | 20 (21.5%) | 15 (7.7%) | | 22 (29.0%) |
| >300 mg/m$^2$ | 45 (48.4%) | 49 (25.3%) | | 27 (35.5%) |
| 1-250 mg/m$^2$ | 21 (22.6%) | 87 (44.9%) | | 27 (35.5%) |
| >250 mg/m$^2$ | 65 (69.9%) | 64 (33.0%) | | 49 (64.5%) |
| Chest Radiation | | | | |
| Chest radiation | 23 (24.7%) | 22 (11.3%) | 0.01 | 47 (61.8%) |
| Age at Cardiomyopathy Diagnosis (years) | | | | |
| Median (range) | 19.4 (0.4-41.7) | — | — | 55 (16-71) |
| Ejection Fraction (%) | | | | |
| Median | 40 (10-56) | 66 (55-81)* | — | 39 (13-50) |

[1]Matching variables. Due to variation in the number of controls per case, the percent of controls and cases in each category of a specific matching variable may not be identical.
*EF available for the 155 controls with anthracycline exposure.
**15 patients with no exposure to anthracyclines received radiation (5 cases, 10 controls).
P values were obtained from conditional logistic regression or generalized linear model taking into consideration the matched set.

Controls had no symptoms/signs of cardiac compromise at study participation, and had normal echocardiographic features (n=155; median EF=66 [55-81]; median SF=37 [29.3-61]) or no echocardiographic examination performed because of lack of cardiotoxic exposure (n=6). Echocardiographic details were not available for 33 anthracycline-exposed controls; their exclusion did not alter and these were included in the analysis.

Risk of Cardiomyopathy:

In a multivariable conditional logistic regression analysis that included age at diagnosis of primary cancer, gender, chest radiation and cumulative anthracycline exposure, the risk of cardiomyopathy for patients exposed to low-to-moderate-dose (1-250 mg/m$^2$), and high-dose (>250 mg/m$^2$) anthracyclines was 5.0 (95% CI, 1.3-20.3, p=0.02) and 33.6 (95% CI, 7.6-149, p<0.001) times higher, respectively (p for trend <0.0001), compared with unexposed patients. Chest radiation was associated with a 5.1-fold increase in cardiomyopathy risk (95% CI, 1.7-15.5, p=0.004).

Genome-Wide Association and Gene-Environment Interaction Analysis.

Figure 13:
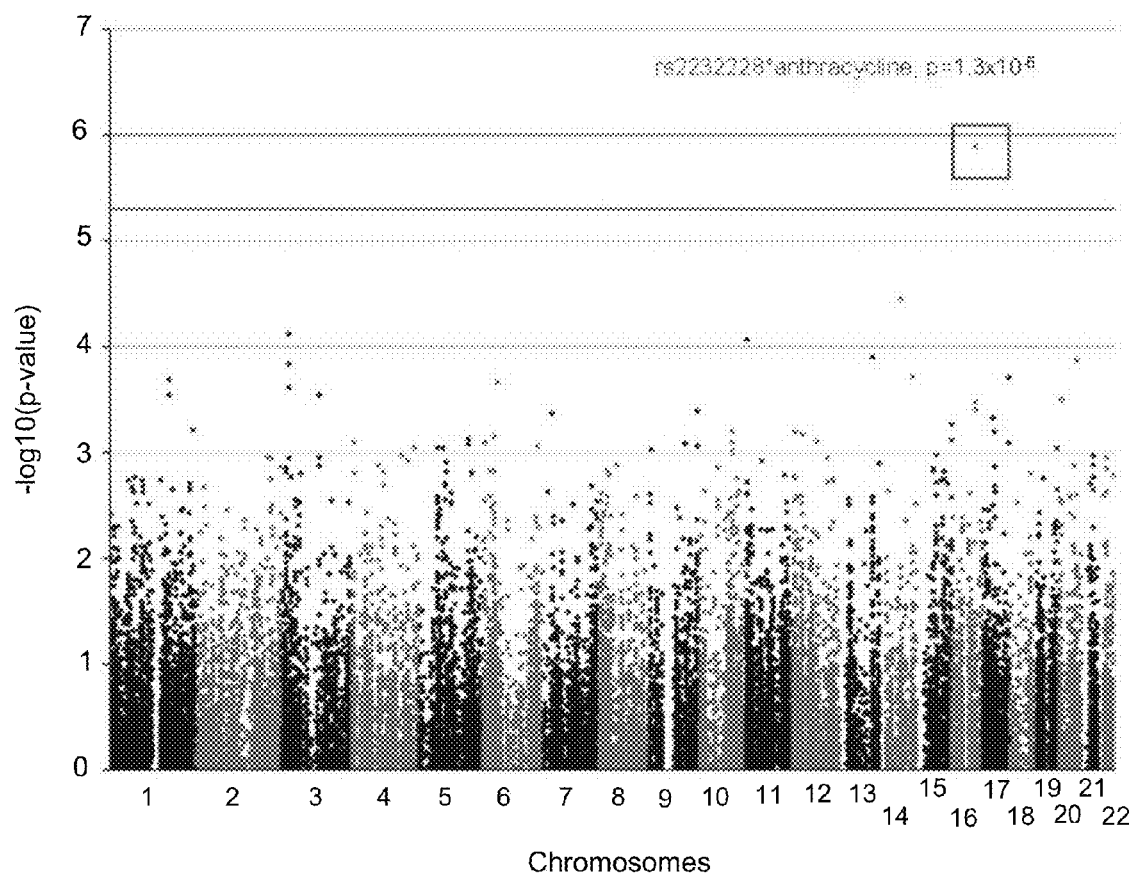
FIG. 13 shows the results of a test for a trend in the Gene-Environment (anthracycline) interaction between cardiomyoapthy and each SNP measured in the GWAS. P values are shown for each SNP measured among the 93 cases with cardiomyoapthy and 194 controls. Analyses are based on 34,912 SNPs (80.64%) on the IBC SNP array. A result above the horizontal red line indicates strong evidence of association at $<5\times10^{-6}$.

Using Model 1, the main effect of SNPs and interaction between each SNP and anthracycline exposure was tested. While no main-effect association was observed between SNPs and cardiomyopathy, one SNP (rs2232228) in gene hyaluronan synthase 3 (HAS3) on chromosome 16 exceeded the multiple-comparison-corrected threshold for significant (p value=1.3×10$^{-6}$, FIG. 13) SNP/anthracycline interaction.

Figure 14:
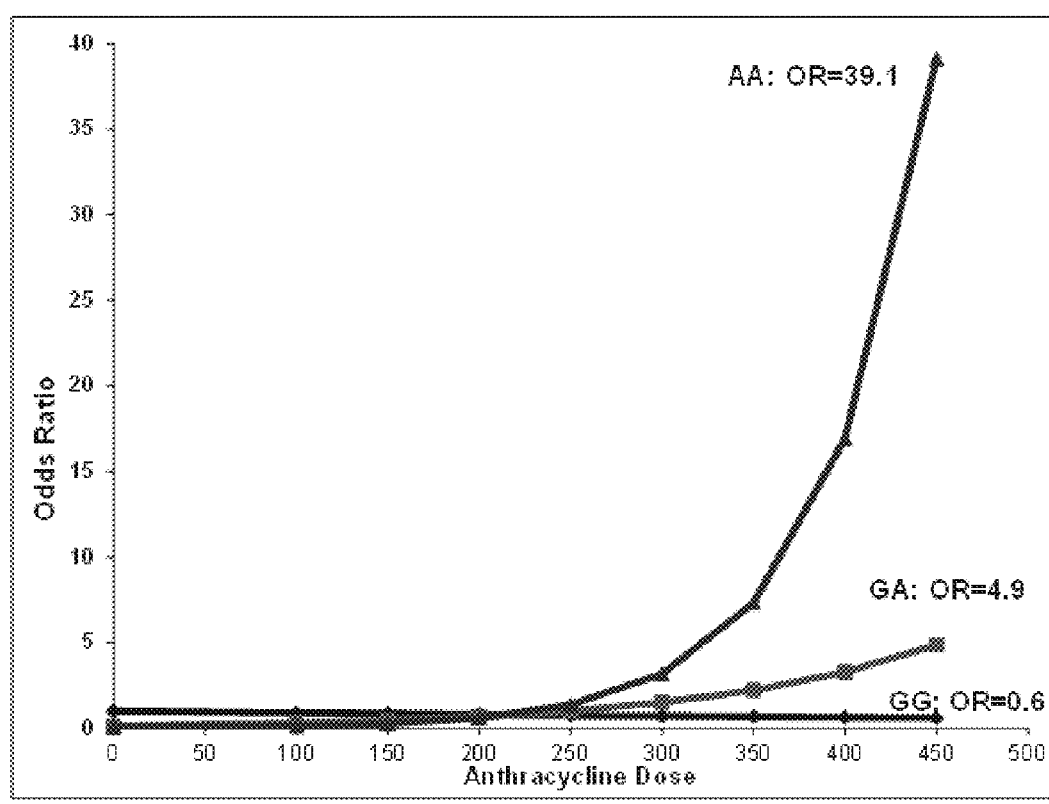
FIG. 14 illustrates the risk of cardiomyopathy by anthracycline dose and genotype status (AA, GA, GG). Odds ratio were calculated based on Model 1, treating anthracycline dose as a continuous variable (reference group: GG genotype with no anthracycline exposure). Exposure to higher doses of anthracycline results in an increase in cardiomyopathy risk for those individuals with AA genotype (AA, triangles).

The modifying effect of rs2232228 genotype on the dose-dependent association between anthracycline and cardiomyopathy risk was shown graphically (FIG. 14) and in a tabular format (Table 5, below). As seen in FIG. 14, at low-to-moderate-dose anthracycline exposure, the risk of cardiomyopathy did not differ significantly by rs2232228 genotype (GG, GA or AA). However, among individuals exposed to higher dose of anthracyclines, the presence of at least one copy of the A allele on SNP rs2232228 increased the cardiomyopathy risk with increasing anthracycline exposure. Especially, in individuals with AA genotype, cardiomypathy risk increased substantially with anthracycline exposure, while in individuals with GG genotype, cardiomyopathy risk was not elevated at any anthracycline dose (FIG. 14). Table 5 shows that among individuals exposed to high-dose anthracyclines, the presence of GA and AA genotypes conferred a 4.2-fold (95% CI, 1.2-14.3, p=0.02) and 8.5-fold (95% CI, 2.0-35.6, p=0.004) increased cardiomyopathy risk, respectively, when compared with the GG genotype. However, among individuals exposed to low-to-moderate-dose anthracyclines, the presence of GA or AA genotype did not confer increased risk.

TABLE 5

Modifying Effect of HAS3 rs2232228 Genotypes on Dose-dependent Risk of Anthracycline-related Cardiomyopathy

| Cumulative Anthracycline exposure | HAS3 rs2232228 genotype status | Risk of cardiomyopathy for all patients* | | Risk of cardiomyopathy stratified by anthracycline exposure (>250 mg/m$^2$)** | |
|---|---|---|---|---|---|
| | | Odds Ratio (95% Confidence Interval) | p-value | Odds Ratio (95% Confidence Interval) | p-value |
| 0-250 mg/m$^2$ | GG | 1.0 | | | |
| | GA | 0.6 (0.19-2.00) | 0.4 | | |
| | AA | 0.2 (0.1-0.95) | 0.04 | | |
| >250 mg/m$^2$ | GG | 1.2 (0.3-5.3) | 0.8 | 1.0 | |
| | GA | 5.1 (1.5-17.2) | 0.008 | 4.2 (1.2-14.3) | 0.02 |
| | AA | 10.3 (2.5-43.3) | 0.001 | 8.5 (2.0-35.6) | 0.004 |

Figure 16:
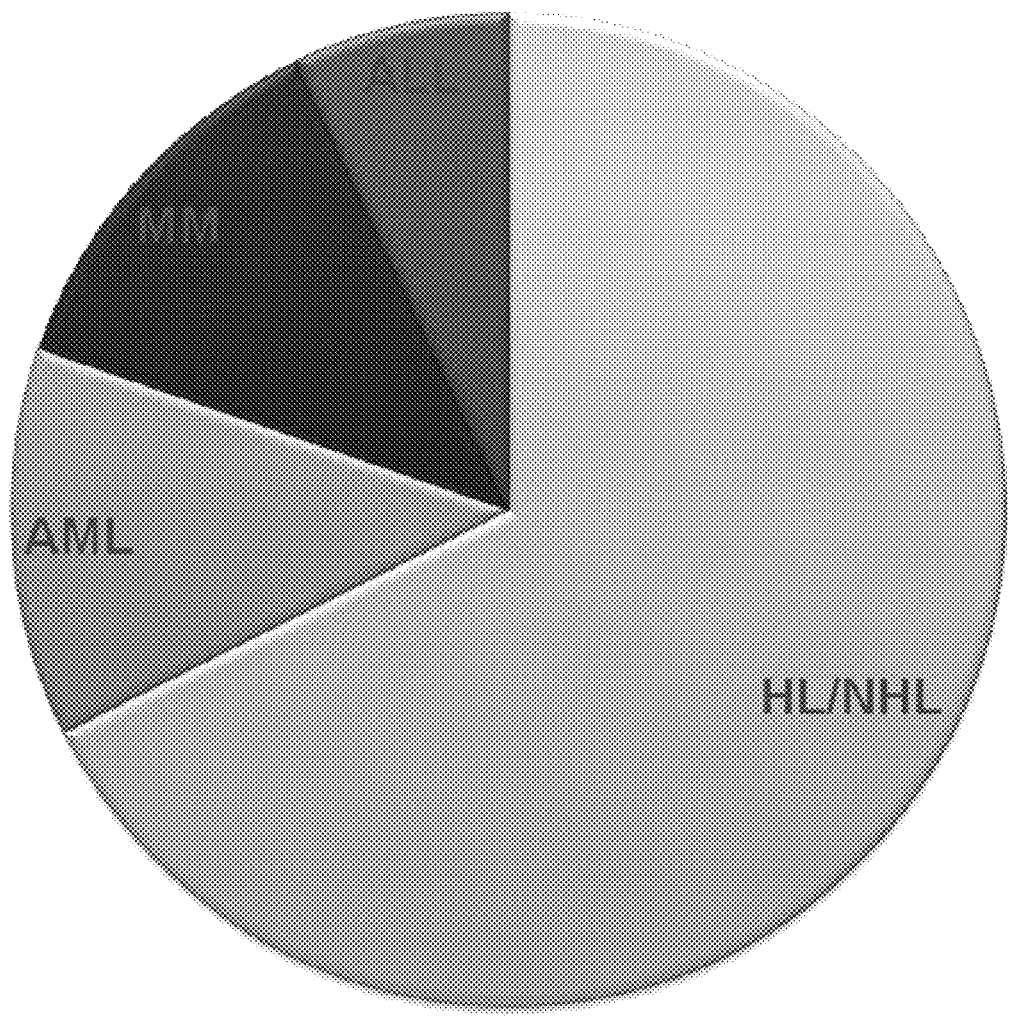
FIG. 16 displays a pie-chart of the different types of cancers found in the patients making up the replication cohort such as Hodgkin's lymphoma/non-Hodgkin's lymphoma (HL/NHL), acute lymphoblastic leukemia (ALL), acute myeloid leukemia (AML), and multiple myeloma (MM).

Odds ratios were obtained from conditional logistic regression adjusting for age at diagnosis, gender, and chest radiation.
*Reference group: 0-250 mg/m$^2$ anthracycline exposure and rs2232228 GG genotype
**Reference group: rs2232228 GG genotype for the >250 mg/m$^2$ anthracycline exposure level Replication Stage
Demographic/Clinical Characteristics:

As shown in Table 4, median age at primary cancer diagnosis for the 76 patients with cardiomyopathy was 48 years (13 to 68) and 59% were non-Hispanic whites. Median cumulative anthracycline exposure was 300 mg/m$^2$ and the median EF was 39% (13%-50%). Patient cases had been treated for Hodgkin's lymphoma/non-Hodgkin's lymphoma, acute lymphoblastic leukemia, acute myeloid leukemia, and multiple myeloma (FIG. 16).

Gene-Environment Interaction Analysis.

Table 6 summarizes the results of gene-environment interaction analysis for SNP rs2232228 using the case-only replication data set. Compared with cases with GG genotype, the odds of cases with AA genotype for being in the high-dose anthracycline group were 5-times higher (95% Cl, 1.2-21.9, p=0.03).

Final Model
Gene-Environment Interaction Analysis.

Cases from the discovery and replication sets were combined to conduct a case-only analysis to test gene-environment interaction at SNP rs2232228. Cases with AA genotype had 4 times higher odds of being in the high-dose anthracyclines group than those with GG genotype (95% Cl, 1.4-11.2, p=0.01, Table 6). Similar results were observed with analysis restricted to non-Hispanic whites (data not shown).

TABLE 6

Case-only Analysis of Gene-Environment Interaction

| HAS3 rs2232228 genotype status | Cumulative Anthracycline Exposure | | | |
|---|---|---|---|---|
| | 1-250 mg/m$^2$ (n [%]) | >250 mg/m$^2$ (n [%]) | OR (95% CI) | P value |
| Replication Set* | | | | |
| GG | 8 (29.6%) | 5 (11.4%) | 1.0 | |
| GA | 11 (40.8%) | 18 (40.9%) | 3.6 (0.8-15.7) | 0.08 |
| AA | 8 (29.6%) | 21 (47.7%) | 5.0 (1.2-21.9) | 0.03 |
| Combined Discovery** and Replication Set | | | | |
| GG | 12 (25.0%) | 11 (10.1%) | 1.0 | |
| GA | 23 (47.9%) | 53 (48.6%) | 2.7 (1.0-7.1) | 0.05 |
| AA | 13 (27.1%) | 45 (41.3%) | 4.0 (1.4-11.2) | 0.01 |

*5 subjects with unknown HAS3 rs2232228 genotype status were excluded.
**Cases of cardiomyopathy in the Discovery set with no anthracycline exposure (n = 7) were excluded from this analysis.
Odds ratios were calculated based on multivariate logistic regression adjusting for age at diagnosis, gender, chest radiation, and race/ethnicity (white vs. other).

Discussion

Hyaluronic acid (HA) is a major component of the extracellular matrix that is expressed in most tissues. HA is especially enriched in matrices undergoing remodeling. HA plays a role in cell proliferation, cell migration, inflammation, tumorigenesis, angiogenesis, embryonic development, and the organization of the extracellular matrix. The dynamic turnover of ECM results in net deposition of matrix in interstitium of affected tissue.

HAS genes (HAS1, HAS2, HAS3) are responsible for HA synthesis. HAS is located in the cell membrane and secreted into interstitial space. Expression of HAS appears to correlate directly to HA synthesis. Regulation of HAS occurs at the level of transcription. HAS1 and HAS2 produce high molecular weight HA. HAS3 gene expression plays an important role in regulation of LMW HA synthesis.

LMW HA accumulates at sites of inflammation and is implicated in multiple proinflammatory activities such as monocyte activation, leukocyte adhesion to endothelium, smooth muscle cell migration as part of wound healing, induction of chemokines, and activation of dendritic cells and macrophages through NF-κB signaling. Additionally, reactive oxygen species have been shown to be potent inducers of HA depolymerization—yielding smaller molecules. HAS3-induced over expression of HA often leads to organ dysfunction. For example, acute lung injury caused by large tidal volume mechanical ventilation is mediated by LMW HA produced by upregulation of HAS3. Thus, these genes may have a role in anthracycline-related myocardial injury through pro-inflammatory activities.

The high-density IBC cardiovascular SNP-array described above was used to study the association between anthracycline-related cardiomyopathy and 34,912 SNPs in 2,100 carefully curated genes known to be associated with de novo cardiovascular disease (Keating et al., 2008). There was a substantial modifying effect of the common SNP rs2232228 in HAS3 on the dose-dependent risk of anthracycline-related cardiomyopathy. Among individuals with a homozygous G genotype on SNP rs2232228, cardiomypathy risk did not demonstrate a dose-dependent increase. However, in individuals with AA genotype, cardiomypathy risk increased significantly as anthracycline exposure increased. Thus, among individuals exposed to high-dose anthracyclines, presence of AA genotype conferred an 8.5-fold increased cardiomyopathy risk, when compared with the GG genotype. This significant gene-environment interaction at SNP rs2232228 was replicated using an independent set of cases with anthracycline-related cardiomyopathy.

In this study, the identified significant SNP rs2232228 on exon2 of HAS3 (67701078 bp) resides on chromosome 16, and appears to be in a region of low LD. The data contain 7 SNPs in HAS3 but the LD between rs2232228 and the other 6 SNPs were not strong (the largest $r^2$ was 0.42— between rs2232228 and rs8047014). The gene-environment interaction for rs8047014 was not significant. The entire chromosome 16 was also imputed using 1000 genome SNPs as reference SNPs. Analysis based on SNPs with imputed $r^2>0.5$ did not reveal any SNPs with strong gene-environment interactions. Finally, the HapMap CEU data was examined within 1 Mb of rs2232228 and only 2 SNPs were identified, both with weak LD (rs8082856 $r^2=0.56$; rs9332431 $r^2=0.579$).

The case-only design used to replicate significant findings is an efficient and valid method for evaluating gene-environment interactions (Begg et al., 1994). A positive association (>2-fold) implies a gene-environment interaction (Vanderweele et al., 2010). The current study demonstrated that, among cases, individuals with homozygosis for A allele of rs223228 in HAS3 had a 5-fold increased odds of being in the high-dose anthracycline group.

Prevalent case-control studies are at risk for underestimation of effect size for genotypes associated with both increased disease risk and disease-associated lethality (Hernan et al., 2004; Anderson et al., 2011). In the current study, a dose-dependent association was not observed between anthracyclines and cardiomypathy risk in individuals with a homozygous G genotype on SNP rs2232228. Although high lethality could erode a potential anthracycline-cardiomyopathy association, there is currently no data to support high lethality associated with the G allele of rs2232228. Furthermore, the replication set included all patients with cardiomyopathy (alive and deceased) in a cohort of HCT recipients. Successful replication of significant findings indicates that survival bias is likely not a significant issue with the prevalent cases and controls in the discovery set.

Of note, while the discovery set was limited to non-Hispanic white childhood cancer survivors, the replication set included cases drawn from survivors of childhood and adult-onset cancer from all racial/ethnic backgrounds. The successful replication of the finding in a clinically and demographically diverse population speaks to the robustness of the association between the common variants in rs2232228 in HAS3 gene and anthracycline-related cardiomyopathy.

In this study, SNP rs2232228 in the HAS3 gene was shown to alter the risk of anthracycline-related cardiomyopathy among patients exposed to high-dose anthracyclines. The IBC cardiovascular SNP-array was used with a carefully-curated yet comprehensive list of genes enriched for their association with de novo cardiovascular disorders, reducing the probability of false-positive associations and helping identify smaller specific pathogenetic regions associated with cardiomyopathy. However, the IBC cardiovascular SNP-array does not include genes that could potentially regulate anthracycline metabolism or disposition (CBR, MRP, MDR1, SLC28A3, ABCB1, ABCB4, ABCC1) (Blanco et al., 2012; Visscher et al., 2012; Wojnowski et al., 2005) or are implicated in the pathogenesis (HFE) (Miranda et al., 2003).

This investigation establishes a foundation to understand the functional significance of SNP rs2232228. In addition, these findings provide a rationale for genotyping for the SNP rs2232228 to tailor anthracycline dose (prior to anthracycline exposure) or develop screening/intervention strategies (after anthracycline exposure) among those at increased risk of cardiomyopathy, in order to maximize the benefits of anthracycline therapy.

REFERENCES

The references, patents and published patent applications listed below, and all references cited in the specification above are hereby incorporated by reference in their entirety, as if fully set forth herein.

Anderson C, Nails M, Biffi A, al. e. The effect of survival bias on case-control genetic association studies of highly lethal diseases. Circ Cardiovasc Genet. 2011; 4:188-96.

Anderson C, Nails M, Biffi A, et al: The effect of survival bias on case-control genetic association studies of highly lethal diseases. Circ Cardiovasc Genet. 4:188-196, 2011.

Armenian S H, Sun C L, Shannon T, al. e. Incidence and Predictors of Congestive Heart Failure Following Autologous Hematopoietic Cell Transplantation. Blood 2011; 118:6023-9.

Bai K J, Spicer A P, Mascarenhas M M, et al. The Role of Hyaluronan Synthase 3 in Ventilator-induced Lung Injury. Am J Respir Crit. Care Med 2005; 172:92-8.

Bains O S, Karkling M J, Lubieniecka J M, et al: Naturally occurring variants of human CBR3 alter anthracycline in vitro metabolism. J Pharmacol Exp Ther 332:755-763, 2010.

Barry E V, Lipshultz S E, Sallan S E. Anthracycline-induced cardiotoxicity: natural history, risk factors, and prevention. In: Am Soc Clin Oncol. Chicago, Ill.; 2008:448.

Begg C B, Zhang Z-F. Statistical analysis of molecular epidemiology studies employing case series. Cancer Epidemiol Biomarkers Prev 1994; 3:173-5.

Blanco J G, Leisenring W M, Gonzalez-Covarrubias V M, et al: Genetic polymorphisms in Blanco J G, Sun C-L, Landier W, al. e. Anthracycline-Related Cardiomyopathy After Childhood Cancer Role of Polymorphisms in Carbonyl Reductase Genes-A report From the Children's Oncology Group. J Clin Oncol 2012; 30:1415-21.

Boucek R J, Olson R D, Brenner D E, et al: The major metabolite of doxorubicin is a potent inhibitor of membrane-associated ion pumps: A correlative study of cardiac muscle with isolated membrane fractions. J Biol Chem 262:15851-15856, 1987.

Bourguignon L Y W, Wong G, Earle C A, Xia W. Interaction of Low Molecular Weight Hyaluronan (LMW-HA) with CD44 and Toll-Like Receptors Promotes the Actin Filament-Associated Protein (AFAP-110)-Actin Binding and MyD88-NFκB Signaling Leading to Pro-inflammatory Cytokine/Chemokine Production and Breast Tumor Invasion. Cytoskeleton (Hoboken) 2011; 68:671-93.

Bryant J, Picot J, Levitt G, al. e. Cardioprotection against the toxic effects of anthracyclines given to children with cancer: a systematic review. Health Technol Assess 2007; 11:1-84.

Bryant J, Picot J, Levitt G, et al: Cardioprotection against the toxic effects of anthracyclines given to children with cancer: A systematic review. Health Technol Assess 11:1-84, 2007.

Burlew B S, Weber K T. Connective tissue and the heart. Functional significance and regulatory mechanisms. Cardiol Clin 2000; 18:435-42.

Cappola T P, Li M, He J, al. e. Common variants in HSPB7 and FRMD4B associated with advanced heart failure. Circulation: Cardiovascular Genet. 2010; 3:147-54.

CBR3 and NQO1 in patients who developed anthracycline-related congestive heart failure after childhood cancer. Cancer 112:2789-2795, 2008.

Gorda S, Samuel J L, Rappaport L. Extracellular matrix and growth factors during heart growth. Heart Fail Rev 2000; 5:119-30.

De Bakker P I, Burtt N P, Graham R R, al. e. Transferability of tag SNPs in genetic association studies in multiple populations. Nat Genet. 2006; 38:1298-303.

Ebert B, Kisiela M, Malatkova P, et al: Regulation of human carbonyl reductase 3 (CBR3; SDR21C2) expression by Nrf2 in cultured cancer cells. Biochemistry 49:8499-8511, 2010.

Forrest G L, Gonzalez B, Tseng W, et al: Human carbonyl reductase overexpression in the heart advances the development of doxorubicin-induced cardiotoxicity in transgenic mice. Cancer Res 60: 5158-5164, 2000.

Gianni L, Herman E H, Lipshultz S E, et al: Anthracycline cardiotoxicity: From bench to bedside. J Clin Oncol 26:3777-3784, 2008.

Gonzalez-Covarrubias V, Zhang J, Kalabus J L, et al: Pharmacogenetics of human carbonyl reductase 1 (CBR1) in livers from black and white donors. Drug Metab Dispos 37:400-407, 2009.

Granowetter L, Womer R, Devidas M, et al: Dose-intensified compared with standard chemotherapy for nonmetastatic Ewing sarcoma family of tumors: A Children's Oncology Group study. J Clin Oncol 27:2536-2541, 2009.

Grenier M A, Lipshultz S. Epidemiology of anthracycline cardiotoxicity in children and adults. Semin Oncol 1998; 25:72-85.

Grier H E, Krailo M D, Tarbell N J, et al: Addition of ifosfamide and etoposide to standard chemotherapy for Ewing's sarcoma and primitive neuroectodermal tumor of bone. N Engl J Med 348:694-701, 2003.

Hellman U, Hellstrom M, Morner S, al. e. Parallel up-regulation of FGF-2 and hyaluronan during development of cardiac hypertrophy in rat. Cell Tissue Res 2008; 332:49-56.

Herna'n M A, Hernandez-Diaz S, Robins J M: A structural approach to selection bias. Epidemiology 15:615-625, 2004.

Hernan M A, Hernandez-Diaz S, Robins J M. A structural approach to selection bias. Epidemiology 2004; 15:615-25.

Jacobson A, Brinck J, Briskin M, Spicer A P, Heldin P. Expression of Human hyaluronan synthases in response to external stimuli. Biochem J 2000; 348:29-35.

Jiang D, Liang J, Fan J, al. e. Regulation of lung injury and repair by Toll-like receptors and hyaluronan. Nat Med 2005; 11:1173-9.

Joerger M, Huitima A D, Meenhorst P L, et al: Pharmacokinetics of low-dose doxorubicin and metabolites in patients with AIDS-related Kaposi sarcoma. Cancer Chemother Pharmacol 55:488-496, 2005.

Johnson S A, Richardson D S: Anthracyclines in haematology: Pharmacokinetics and clinical studies. Blood Rev 12:52-71, 1998.

Kalabus J L, Sanborn C C, Jamil R G, et al: Expression of the anthracycline-metabolizing enzyme carbonyl reductase 1 in hearts from donors with Down syndrome. Drug Metab Dispos 38:2096-2099, 2010.

Keating B J, Tischfield S, Murray S S, et al. Concept, design and implementation of a cardiovascular gene-centric 50 k SNP array for large-scale genomic association studies. PLoS ONE 2008; 3:e3583.

Knudson C B, Knudson W. Hyaluronan-binding proteins in development, tissue homeostasis and disease. FASEB J 1993; 7:1233-41.

Kremer L C M, Caron H N: Anthracycline cardiotoxicity in children. N Engl J Med 351:120 121, 2004.

Kremer L C M, van der Pal H J H, Offring a M, et al: Frequency and risk factors of subclinical cardiotoxicity after anthracycline therapy in children: A systematic review. Ann Oncol 13:819-829, 2002.

Lakhman S S, Chen X, Gonzalez-Covarrubias V, et al: Functional characterization of the promoter of human carbonyl reductase 1 (CBR1): Role of XRE elements in mediating the induction of CBR1 by ligands of the aryl hydrocarbon receptor. Mol Pharmacol 72:734-743, 2007.

Lakhman S S, Ghosh D, Blanco J G: Functional significance of a natural allelic variant of human carbonyl reductase 3 (CBR3). Drug Metab Dispos 33:254-257, 2005.

Laurent T C, Fraser J R E. Hyaluronan. FASEB J 1992; 6:2397-404.

Lehmann S, Isberg B, Ljungman P, et al: Cardiac systolic function before and after hematopoietic stem cell transplantation. Bone Marrow Transplant 26:187-192, 2000.

Lipshultz S E, Lipsitz S R, Sallan S E, et al: Chronic progressive cardiac dysfunction years after doxorubicin therapy for childhood acute lymphoblastic leukemia. J Clin Oncol 23:2629-2636, 2005.

McKee C M, Penno M B, Cowman M, et al. Hyaluronan (HA) fragments induce chemokine gene expression in alveolar macrophages. The role of HA size and CD44. Clin Invest 1996:2403-13.

Meissner K, Sperker B, Karsten C, al. e. Expression and localization of P glycoprotein in human heart: Effects of cardiomyopathy. J Histochem Cytochem 2002; 50:1351-6.

Menna P, Salvatorelli E, Minotti G: Cardiotoxicity of antitumor drugs. Chem Res Toxicol 21:978-989, 2008.

Minotti G, Menna P, Salvatorelli E, et al: Anthracyclines: Molecular advances and pharmacologic developments in antitumor activity and cardiotoxicity. Pharmacol Rev 56:185-229, 2004.

Miranda C J, Makui H, Soares R J, al. e. Hfe deficiency increases susceptibility to cardiotoxicity and exacerbates changes in iron metabolism induced by doxorubicin. Blood 2003 2003; 102:2574-80.

Mordente A, Meucci E, Silvestrini A, et al: New developments in anthracycline-induced cardiomyopathy. Curr Med Chem 16:1656-1672, 2009.

Mordente A, Minotti G, Martorana G E, et al: Anthracycline secondary alcohol metabolite formation in human or rabbit heart: Biochemical aspects and pharmacologic implications. Biochem Pharmacol 66:989-998, 2003.

Mrabat H, Beagle J, Hang Z, Garg H G, Hales C A, Quinn D A. Inhibition of HA synthase 3 mRNA expression, with a phosphodiesterase 3inhibitor, blocks lung injury in a septic ventilated rat model. Lung 2009:233-9.

Mulrooney D A, Yeazel M W, Kawashima T, al. e. Cardiac outcomes in a cohort of adult survivors of childhood and adolescent cancer: retrospective analysis of the Childhood Cancer Survivor Study cohort. BMJ 2009; 339:b4606.

Mulrooney D A, Yeazel M W, Kawashima T, et al: Cardiac outcomes in a cohort of adult survivors of childhood and adolescent cancer: Retrospective analysis of the Childhood Cancer Survivor Study cohort. BMJ 339:b4606, 2009.

Mushlin P S, Cusack B J, Boucek R J, et al: Time-related increases in cardiac concentrations of doxorubicinol could interact with doxorubicin to depress myocardial contractile function. Br J Pharmacol 110:975-982, 1993.

Noble P W, McKee C M, Cowman M, Shin H S. Hyaluronan fragments activate an NF-kappa B/!-kappa B alpha auto-regulatory loop in murine macropahges. J Exp Med 1996; 183:2373-8.

Olson L E, Bedja D, Alvey S J, et al: Protection from doxorubicin-induced cardiac toxicity in mice with a null allele of carbonyl reductase 1. Cancer Resn 63:6602-6606, 2003.

Olson R D, Mushlin P S, Brenner D E, et al: Doxorubicin cardiotoxicity may be caused by its metabolite, doxorubicinol. Proc Natl Acad Sci USA 85:3585-3589, 1988.

Perik P, Vries E G, Gietema J A, et al. The dilemma of the strive for apoptosis in oncology: mind the heart. Crit. Rev Oncol Hematol 2005; 53:101-13.

Puma N, Ruggiero A, Ridola V, et al. Anthracycline-related cardiotoxicity: risk factors and therapeutic options in childhood cancers. SIGNA VITAE 2008; 3:30-4.

Purcell S, Neale B, Todd-Brown K, al. e. PLINK: a tool set for whole-genome association and population-based linkage analyses. Am J Hum Genet. 2007; 81:559-75.

R. project: (accessed at http://www.r-project.org/).

Shankar S M, Marina N, Hudson M M, et al. Monitoring for cardiovascular disease in survivors of childhood cancer: report from the Cardiovascular Disease Task Force of the Children's Oncology Group. Pediatrics 2008; 121:e387-96.

Spicer P, Tien J Y. Hyaluronan and morphogenesis. Birth defects Res C embryo Today 2004; 72:89-108.

Stewart D J, Grewaal D, Green R M, et al: Concentrations of doxorubicin and its metabolites in human autopsy heart and other tissues. Anticancer Res 13:1945-1952, 1993.

Toole B P. Hyaluronan and its binding proteins, the hyaladherins. Curr Opin Cell Biol 1990; 2:839-44.

van Dalen E C, van den Brug M, Caron H N, et al: Anthracycline-induced cardiotoxicity: comparison of recommendations for monitoring cardiac function during therapy in paediatric oncology trials. Eur. J. Cancer 42:3199-3205, 2006.

Vanderweele T J, Hernandez-Diaz S, Hernan M A. Case-only gene-environment interaction studies: when does association imply mechanistic interaction. Genet Epidemiol 2010; 34:327-34.

Visscher H, Ross C J D, Rassekh S R, al. e. Pharmacogenetic prediction of anthracycline-induced cardiotoxicity in children. J Clin Oncol 2012; 30:1422-28.

Waldenstrom A, Martinussen H J, Gerdin B, Hallgen R. Accumulation of hyaluronan and tissue edema in experimental myocardial infarction. J Clin Invest 1991; 88:1622-8.

West D C, Hampson I N, Arnold F, Kumar S. Angiogenesis induced by degradation products of hyaluronic acid. Science 1985; 228:1324-6.

Wojnowski L, Kulle B, Schirmer M, al. e. NAD(P)H oxidase and multidrug resistance protein genetic polymorphisms are associated with doxorubicin-induced cardiotoxicity. Circulation 2005; 112:3754-62.

Wouters K A, Kremer L C M, Miller T L, et al: Protecting against anthracycline-induced myocardial damage: A review of the most promising strategies. Br J Haematol 131:561-578, 2005.

Zhang J, Blanco J G: Identification of the promoter of human carbonyl reductase 3 (CBR3) and impact of common promoter polymorphisms on hepatic CBR3 mRNA expression. Pharm Res 26: 2209-2215, 2009.

Zhang W, Watson C E, Liu C, Williams K J, Werth V P. Glucocorticoids induce a near-total suppression of hyaluronan synthase mRNA in dermal fibroblasts and in osteoblasts: a molecular mechanism contributing to organ atrophy. Biochem J 2000; 349:91-7.

What is claimed is:

1. A method for optimally administering an anthracycline to a cancer patient to prevent cardiotoxicity comprising:
    genotyping a cancer patient using a whole genome or locus specific method to determine at least one copy of SNP rs2232228 (G>A) within an HAS3 gene, and optimally administering a therapeutically effective dose of the anthracycline to the patient, wherein the therapeutically effective dose comprises a cumulative dose of approximately 1-250 mg/m$^2$.

2. The method of claim 1, wherein the therapeutically effective dose comprises a cumulative dosage of approximately 1-150 mg/m$^2$ when the cancer patient carries two copies of the SNP rs2232228(G>A).

3. The method of claim 1, wherein the anthracycline is doxorubicin, daunomycin, epirubicin, mitoxantrone, valrubicin, or idarubicin.

4. The method of claim 1, wherein the anthracycline is administered in combination with one or more additional chemotherapeutics or cardioprotectants.

5. The method of claim 1, wherein the cardiotoxicity prevented is cardiomyopathy or congestive heart failure (CHF).

6. A method of preventing anthracycline-induced cardiomyopathy in a cancer patient comprising:
    genotyping a cancer patient using a whole genome or locus specific method to determine at least one copy of SNP rs2232228 (G>A) within an HAS3 gene, and optimally administering a therapeutically effective dose of an anthracycline to the patient, wherein the therapeutically effective dose is a low or moderate dose.

7. The method of claim 6, wherein the patient has one copy of the SNP rs2232228(G>A) and the effective dose is a cumulative dosage of approximately 1-250 mg/m$^2$.

8. The method of claim 6, wherein the patient has two copies of the SNP rs2232228(G>A) and the effective dose is a cumulative dosage of approximately 1-150 mg/m$^2$.

9. The method of claim 6, wherein the anthracycline is doxorubicin, daunomycin, epirubicin, mitoxantrone, valrubicin, or idarubicin.

10. The method of claim 6, wherein the anthracycline is administered in combination with one or more additional chemotherapeutics or cardioprotectants.

* * * * *